United States Patent [19]
Hawkins

[11] Patent Number: 5,952,285
[45] Date of Patent: Sep. 14, 1999

[54] CONCENTRATED AQUEOUS SURFACTANT COMPOSITIONS

[75] Inventor: John Hawkins, Cleator Moor, United Kingdom

[73] Assignee: Albright & Wilson Limited, West Midland, United Kingdom

[21] Appl. No.: 08/866,399

[22] Filed: May 30, 1997

Related U.S. Application Data

[63] Continuation of application No. 08/684,327, Jul. 19, 1996, abandoned, which is a continuation of application No. 08/502,364, Jul. 14, 1995, abandoned, which is a continuation of application No. 08/316,061, Sep. 30, 1994, abandoned, which is a continuation of application No. 08/119,419, Sep. 10, 1993, abandoned, which is a continuation-in-part of application No. 07/783,369, Oct. 28, 1991, abandoned, application No. 07/938,426, Aug. 31, 1992, abandoned, and application No. 07/683,337, Apr. 10, 1991, abandoned, said application No. 07/783,369, is a continuation-in-part of application No. 07/683,337, said application No. 07/938,426, is a continuation-in-part of application No. 07/783,369.

[30] Foreign Application Priority Data

| Apr. 10, 1990 | [GB] | United Kingdom | .................. 9008120 |
| Mar. 19, 1991 | [GB] | United Kingdom | .................. 9105788 |
| Aug. 30, 1991 | [GB] | United Kingdom | .................. 9118564 |
| Oct. 18, 1991 | [GB] | United Kingdom | .................. 9122213 |

[51] Int. Cl.$^6$ ................ C11D 1/83; C11D 3/10; C11D 17/00
[52] U.S. Cl. .................. 510/405; 510/337; 510/340; 510/343; 510/352; 510/425; 510/428; 510/498; 510/509
[58] Field of Search ..................... 510/337, 340, 510/343, 351, 352, 405, 418, 425, 428, 498, 507, 509

[56] References Cited

U.S. PATENT DOCUMENTS

| 3,346,873 | 10/1967 | Herrmann | 252/137 |
| 4,515,704 | 5/1985 | Akred et al. | 252/135 |
| 4,559,169 | 12/1985 | Wevers et al. | 252/543 |
| 4,618,446 | 10/1986 | Haslop et al. | 252/135 |
| 4,659,497 | 4/1987 | Akred et al. | 252/135 |
| 4,793,943 | 12/1988 | Haslop et al. | 252/135 |
| 4,810,409 | 3/1989 | Harrison et al. | 252/102 |
| 4,839,077 | 6/1989 | Cramer et al. | 252/98 |
| 4,871,467 | 10/1989 | Akred et al. | 252/135 |
| 5,021,195 | 6/1991 | Machin et al. | 252/545 |
| 5,039,451 | 8/1991 | Phillips et al. | 252/356 |
| 5,198,353 | 3/1993 | Hawkins et al. | 435/188 |

FOREIGN PATENT DOCUMENTS

| 0068520 | 1/1983 | European Pat. Off. |
| 0354010 | 2/1990 | European Pat. Off. |

*Primary Examiner*—Lorna Douyon
*Attorney, Agent, or Firm*—Frishauf, Holtz, Goodman, Langer & Chick. P.C.

[57] ABSTRACT

A liquid detergent composition containing water; surfactant in a concentration which would in the absence of electrolyte form a pourable hexagonal, or cubic phase at 20° C.; and sufficient dissolved electrolyte to form a substantially Newtonian or optically isotropic liquid.

2 Claims, 18 Drawing Sheets

CONCENTRATED AQUEOUS SURFACTANT COMPOSITIONS

This application is a Continuation of application Ser. No. 08/684,327, filed Jul. 19, 1996, abandoned, which is a continuation of Ser. No. 08/502,364 filed Jul. 14, 1995, abandoned, which is a continuation application of Ser. No. 08/316,061, filed Sep. 30, 1994, abandoned, which is a continuation of application Ser. No. 08/119,419, filed Sep. 10, 1993, abandoned, which is a Continuation-in-Part of application Ser. No. 07/783,369 filed Oct. 28, 1991, abandoned, and of application Ser. No. 07/938,426, filed Aug. 31, 1992, abandoned, and of application Ser. No. 07/683,337, filed Apr. 10, 1991 abandoned; and wherein application Ser. No. 07/783,369, abandoned, is a Continuation-In-Part of application Ser. No. 07/683,337, abandoned; and application Ser. No. 07/938,426, filed Aug. 31, 1992, abandoned, is a Continuation-In-Part of application Ser. No. 07/783,369, filed Oct. 28, 1991 abandoned.

BACKGROUND OF THE INVENTION

The invention relates to concentrated aqueous based surfactant compositions and especially to liquid laundry detergent compositions and toiletry compositions containing high concentrations of surfactant.

Liquid laundry detergents have a number of advantages compared with powders which have led to their taking a substantial proportion of the total laundry detergent market. The introduction of compact powders containing higher concentrations of active ingredient than the traditional powders has challenged the trend towards liquids. There is a market requirement for more concentrated liquids to meet this challenge, and in particular concentrated aqueous surfactant compositions containing dissolved or suspended builder salts.

The ability to concentrate liquid detergent has hitherto been limited by the tendency of conventional detergent surfactant systems to form mesophases at concentrations above 30% by weight, based on the weight of water and surfactant. Mesophases, or liquid crystal phases are phases which exhibit a degree of order less than that of a solid but greater than that of a classical liquid, e.g. order in one or two, but not all three dimensions.

Up to about 30% many surfactants form micellar solutions ($L_1$-phase) in which the surfactant is dispersed in water as micelles, which are aggregates of surfactant molecules, too small to be visible through the optical microscope. Micellar solutions look and behave for most purposes like true solutions. At about 30% many detergent surfactants form an M-Phase, which is a liquid crystal with a hexagonal symmetry and is normally an immobile, wax-like material. Such products are not pourable and obviously cannot be used as liquid detergents. At higher concentrations, e.g. above about 50% by weight, usually over some concentration range lying above 50% and below 80% a more mobile phase, the G-phase, is formed.

G-phases are non-Newtonian (shear thinning) normally pourable phases, but typically have a viscosity, flow characteristic and cloudy, opalescent appearance, which render them unattractive to consumers and unsuitable for use directly as laundry detergents. Attempts to suspend solids in G-phases have been unsuccessful, giving rise to products which are not pourable.

At still higher concentrations e.g. above about 70 or 80% most surfactants form a hydrated solid. Some, especially non-ionic surfactants, form a liquid phase containing dispersed micelle size droplets of water ($L_2$-phase). $L_2$ phases have been found unsuitable for use as liquid detergents because they do not disperse readily in water, but tend to form gels. Other phases which may be observed include the viscous isotropic (VI) phase which is immobile and has a vitreous appearance.

The different phases can be recognised by a combination of appearance, rheology, textures under the polarising microscope, electron microscopy and X-ray diffraction or neutron scattering.

The following terms may require explanation or definition in relation to the different phases discussed in this specification: "Optically isotropic" surfactant phases do not normally tend to rotate the plane of polarisation of plane polarised light. If a drop of sample is placed between two sheets of optically plane polarising material whose planes of polarisation are at right angles, and light is shone on one sheet, optically isotropic surfactant samples do not appear substantially brighter than their surroundings when viewed through the other sheet. Optically anisotropic materials appear substantially brighter. Optically anisotropic mesophases typically show characteristic textures when viewed through a microscope between crossed polarisers, whereas optically isotropic phases usually show a dark, essentially featureless continuum.

"Newtonian liquids" have a viscosity which remains constant at different shear rates. For the purpose of this specification, liquids are considered Newtonian if the viscosity does not vary substantially at shear rates up to 1000 $sec^{-1}$.

"Lamellar" phases are phases which comprise a plurality of bilayers of surfactant arranged in parallel and separated by liquid medium. They include both solid phases and the typical form of the liquid crystal G-phase. G-phases are typically pourable, non-Newtonian, anisotropic products. They are typically viscous-looking, opalescent materials with a characteristic "smeary" appearance on flowing. They form characteristic textures under the polarising microscope and freeze fractured samples have a lamellar appearance under the electron microscope. X-ray diffraction or neutron scattering similarly reveal a lamellar structure, with a principal peak typically between 4 and 10 nm, usually 5 to 6 nm. Higher order peaks, when present occur at double or higher integral multiples of the Q value of the principal peak. Q is the momentum transfer vector and is related, in the case of lamellar phases, to the repeat spacing d by the equation Q=2n[pi]/d where n is the order of the peak.

G-phases, however, can exist in several different forms, including domains of parallel sheets which constitute the bulk of the typical G-phases described above and spherulites formed from a number of concentric spheroidal shells, each of which is a bilayer of surfactant. In this specification the term "lamellar" will be reserved for compositions which are at least partly of the former type. Opaque compositions at least predominantly of the latter type in which the continuous phase is a substantially isotropic solution containing dispersed spherulites are referred to herein as "spherulitic". Compositions in which the continuous phase comprises non-spherulitic bilayers usually contain some spherulites but are typically translucent, and are referred to herein as "G-phase compositions". G-phases are sometimes referred to in the literature as Lα phases.

$L_1$-phases are mobile, optically isotropic, and typically Newtonian liquids which show no texture under the polarising microscope. Electron microscopy is capable of resolving the texture of such phases only at very high magnifications, and X-ray or neutron scattering normally gives only a single broad peak typical of a liquid structure, at very small angles close to the reference beam. The viscosity of an $L_1$-phase is usually low, but may rise significantly as the concentration approaches the upper phase boundary.

M-phases are typically immobile, anisotropic products resembling waxes. They give characteristic textures under the polarising microscope, and a hexagonal diffraction pattern by X-ray or neutron diffraction which comprises a major peak, usually at values corresponding to a repeat spacing between 4 and 10 nm, and sometimes higher order peaks, the first at a Q value which is $3^{0.5}$ times the Q value of the principal peak and the next double the Q value of the principal peak. M-phases are sometimes referred to in the literature as H-phases.

VI-phases have a cubic symmetry exhibiting peaks at $2^{0.5}$ and $3^{0.5}$ times the Q value of the principal peak, under X-ray diffraction or neutron scattering. They are typically immobile, often transparent, glass like compositions. They are sometimes observed over a narrow range of concentrations, typically just below those at which the G-phase is formed.

The term "pourable hexagonal phase" is used herein to describe a phase exhibiting certain characteristic properties which include: pourability, often with an appreciable yield point, and a viscous, mucus-like characteristic and sometimes a lamellar flow pattern, resembling those normally observed with a "G" phase; birefringence; and a hexagonal symmetry typical of an M-phase, by small angle X-ray diffraction or neutron scattering. Some of these compositions tend to separate on prolonged standing into two layers, one of which is substantially clear, optically isotropic and substantially Newtonian in behaviour and the other an M-phase or G-phase.

Optical microscopy using crossed polars or differential interference contrast, typically reveals textures which may resemble either M-phase or G-phase or be intermediate, or alternate between the two on application and relaxation of shear. GB 2179054 and GB 2179053 describe compositions (eg, in the comparative examples) which appear to be in the pourable hexagonal phase.

The pourable hexagonal phase should be distinguished from aerated M-phase. Conventional M-phases containing substantial amounts of entrained air may sometimes exhibit properties similar to those described above as being characteristic of the pourable hexagonal phase. The former however revert to conventional non-pourable M-phases when de-aerated, eg, by centrifuging. The pourable hexagonal phases as herein defined exhibit the aforesaid properties even when substantially free from entrained air.

One possible explanation for the properties of pourable hexagonal phases is that they are compositions which exist normally in the M-phase but which are very close to either the M/G phase boundary or the $L_1$/M boundary (or which exhibit a broad, indistinct M/G or $L_1$/G phase boundary region), so that shear stresses convert them to G-phases. The pourable hexagonal phases are typically more dilute than conventional G-phases which typically occur at active concentrations above 50%, usually 60 to 80%. They are also more viscous in appearance than the G-phases which normally occur in the lower part of the above typical range.

$L_2$-phases resemble $L_1$-phases in general appearance but are less easily diluted with water.

A detailed description, with illustrations, of the different textures observable using a polarising microscope, which characterise the different mesophases, is to be found in the classic paper by Rosevear JAOCS Vol. 31 P.628.

All references herein to the formation or existance of specific phases or structures are to be construed, unless the context requires otherwise, as references to their formation or existence at 20° C.

For the purpose of this specification "an electrolyte" means any water soluble compound which is not a surfactant and which ionises in solution. Preferred are electrolytes which tend to salt a surfactant out of solution when each is present in sufficiently high concentration, which are referred to herein as "surfactant-desolubilising electrolytes".

"Builder" is used herein to mean a compound which assists the washing action of a surfactant by ameliorating the effects of dissolved calcium and/or magnesium. Generally builders also help maintain the alkalinity of wash liquor. Typical builders include sequestrants and complexants such as sodium tripolyphosphate, potassium pyrophosphate, trisodium phosphate, sodium citrate or sodium nitrilotriacetate, ion exchangers such as zeolites and precipitants such as sodium or potassium carbonate and such other alkalis as sodium silicate.

Detergents for laundry use normally contain a surfactant and a builder. The latter helps the surfactant to perform much more efficiently, thereby substantially reducing the amount of surfactant needed. Built liquid detergents contain about 5 to 15% of surfactant and 10 to 30% of builder.

In the absence of builder more than double the amount of surfactant may be required to obtain acceptable performance. Since the surfactant is considerably more expensive than the builder, the latter has been considered by some essential to cost effective performance.

The major problem with trying to include soluble builders in liquid detergents has been that such builders are electrolytes which tend to salt surfactants out of solution. The normal consequence of adding a salting-out electrolyte to an aqueous solution of an organic compound is to cause phase separation. This has commonly been observed in the case of aqueous surfactants and has given rise to a strong prejudice against adding electrolytes even to weak concentrations of aqueous surfactant in high enough concentrations to incur the likelihood of salting out. In the case of more strongly concentrated aqueous surfactant solutions, there has been an even stronger prejudice against adding electrolyte in any significant amount.

Typically commercial liquid laundry detergents fall into three main categories. The original liquid laundry detergents were aqueous surfactants, containing no more than low concentrations of water-soluble builder salts together with solvents and hydrotropes in order to overcome the salting effect of any electrolyte and maintain a stable, non-structured, isotropic, aqueous, micellar solution ($L_1$-phase). The performance of such products has been poor compared with powders. The performance per gram of product has been improved by formulating them at relatively high concentrations, e.g. up to 60% surfactant by use of more soluble, but more expensive surfactants in conjunction with sufficiently high levels of organic solvent. Because the latter do not contain high levels of builder they have to be dosed at higher levels than those which have customarily been needed for standard built products, in order to obtain comparable performance. The effect is to provide higher levels of surfactant in the wash liquor to compensate for the lack of builder. In addition the more soluble surfactants tend to be less effective as detergents. There is therefore little benefit in terms of the bulk required, and the disadvantage of a relatively high cost per wash, exacerbated by the higher cost of the soluble surfactants and the cost of solvent which is needed to maintain a homogeneous isotropic composition, but which does not contribute to wash performance. The high surfactant loading per wash and the presence of solvent is also disadvantageous on environmental grounds.

Progress from the early type of low-builder, clear liquids was for many years prevented by the knowledge that if the concentration of electrolyte salt is too high phase separation is observed. However it has been shown, e.g. in U.S. Pat. No. 4,515,704, U.S. Pat. No. 4,659,497, U.S. Pat. No. 4,871,467, U.S. Pat. No. 4,618,446 or U.S. Pat. No. 4,793, 943 that when electrolyte is added to aqueous surfactants in concentrations substantially greater than the minimum concentration required to salt out any surfactant, then provided that there is enough of the latter present, instead of phase separation, a structured dispersion of surfactant in aqueous electrolyte is formed which may be stable and usually resembles either an emulsion or a gel.

This discovery led to the development of a second type of liquid detergent which comprised a suspension of solid builder, such as sodium tripolyphosphate or zeolite, in a structured aqueous surfactant. The surfactant structure is usually formed by the interaction of dissolved electrolyte with the surfactant. The latter is salted out of the isotropic micellar phase to form a mesophase interspersed with the aqueous electrolyte.

By suitable choice of electrolyte and surfactant concentration a stable mobile composition can be obtained, which maintains the solid particles of builder in suspension indefinitely. Because the builder level is high, the performance of this type of detergent at low surfactant level is good, giving a relatively low cost per wash, and environmental benefits from reduced usage of surfactant.

However the most effective solid builders have themselves been attacked an environmental grounds and are restricted or banned in some countries. Typical built liquid detergents have the further disadvantage of being relatively dilute, with surfactant concentrations typically in 5 to 15% range. This means that the consumer has to carry home a substantial bulk of product. Few attempts to increase the concentration of surfactant in the structured type of liquid detergent above about 20% have been made for fear of phase separation or unacceptable viscosity. Because the prejudice against adding electrolyte to concentrated surfactant is so strong the possibility of formulating aqueous pourable detergents with high surfactant levels and high levels of dissolved electrolyte has not been seriously considered as a practical possibility.

The third type of detergent, and the most recent to be introduced onto the market is an anhydrous type. This has the advantage of high surfactant concentration and also the possibility of including oxidising bleach which is normally difficult to include in aqueous formulations. However existing anhydrous formulations contain substantial amounts of organic solvent, which may be criticised on environmental grounds, and are difficult to dilute to wash liquor concentration. Addition of water tends to cause gel formation. The high concentration can give rise to a risk of overdosing. In addition the storage stability of this type of detergent is usually poor.

It is an object of the invention to prepare highly concentrated aqueous based structured liquid detergent or toiletry compositions which do not require the presence of solvents but which may contain high levels of surfactant that have only been available hitherto in solvent containing formulations. A particular object is to provide such compositions which are capable of suspending particles of solid or liquid, such as toiletry ingredients or builder. A further object is to provide mobile compositions containing high levels of surfactant and high concentrations of soluble builder. A further object is to provide concentrated detergents which are easily diluted to wash concentrations, without gel formation. It is also an object of the invention to provide aqueous structured surfactants capable of suspending functional solids such as pesticides, abrasives, dyes, weighting agents and the like.

Another object of the invention is to provide a liquid detergent which contains a high total payload of surfactant and builder.

The aim is to provide detergents that can be easily diluted to give stable and preferably clear semi-concentrated solutions which are readily dosed. Such compositions, would overcome the principal disadvantages of each of the three types of liquid laundry detergent currently on the market.

A further object is to formulate such detergents using surfactants based on renewable resources.

A further object of the invention is to permit the formulation of toiletry compositions containing suspended solids and water immiscible liquid. The stable suspension of various ingredients which are useful in toiletry, cosmetic, shampoo and topical pharmaceutical preparations has long been a goal of formulators. Hitherto this has proved difficult because the surfactants which are preferred for toiletry use have not been obtained as solid-suspending structures. Attempts to suspend solids by the use of polymers, clays and similar thickening agents add to the cost of the product without contributing to performance.

Currently available structured liquid detergents are typically based on alkyl benzene sulphonate, in admixture with smaller amounts of alkyl ether sulphate and/or alkyl sulphate and/or non-ionic surfactants such as alcohol ethoxylates, and/or mono or diethanolamides. Such mixtures are unsuitable for toiletry use. Attempts to formulate highly concentrated suspensions using these systems, based on existing technology have been unsuccessful. Such mixtures, typically have a relatively high cloud point and are relatively insoluble in dilute aqueous electrolyte solution.

This indicates that they are comparatively easily forced into a solid-suspending structure by electrolyte. In solution they form clear, isotropic, mobile $L_1$ micellar solutions at concentrations up to about 30% by weight. At higher concentrations they form immobile M-phases, and at still higher concentrations G-phases and VI-phases may be observed.

When electrolyte is added progressively to conventional $L_1$ surfactant systems of the above type, a sequence is observed which is described in U.S. Pat. No. 4,618,446. Initially, if the surfactant is sufficiently dilute, e.g. below about 30% by weight, a clear, isotropic, micellar solution is formed. Addition of electrolyte at first causes an increase in conductivity.

Further additions cause turbidity due to the formation of surfactant spherulites which separate on standing to leave a clear aqueous layer containing electrolyte and an opaque surfactant layer. It is envisaged that the spherulites form by the deposition of successive bilayers of salted-out surfactant on the spherical micelles present in the $L_1$-phase.

With further additions of electrolyte the spherulites become more numerous. They form clusters separated by clear areas. The proportion of the surfactant layer formed on separation increases, while the electrical conductivity falls.

Eventually a packed mass of spherulites is formed with no visible clear areas. The composition no longer undergoes separation, but remains homogeneous and opaque, even on prolonged standing. At this stage the composition is highly structured with a marked yield point and can suspend solid particles indefinitely.

After further additions of electrolyte the electrical conductivity passes through a minimum and then rises. At the same time the average size of the spherulites declines while their number appears to be approximately constant. Clear areas appear again and the system is no longer solid-suspending.

Subsequently, if the dissolved electrolyte concentration is increased further, the conductivity may pass through a further point of inflexion and falls again to a second minimum. The second minimum is associated with the formation of an open lamellar structure which is believed to comprise a reticular lamellar phase forming a three dimensional network interspersed with a substantially surfactant-free aqueous electrolyte solution (often referred to as a lye phase).

Thus in the classical built liquid detergents two types of suspending system can be distinguished.

I. A spherulite system, associated with a first (lower electrolyte) trough in the plot of conductivity against dissolved electrolyte concentration, is at its most stable near the first conductivity minimum. It comprises spherulites which range typically between 0.1 and 20 microns in size and each having an onion like structure comprising a series of concentric spherical layers, each layer consisting of a bilayer of surfactant separated from neighbouring layers by an intermediate spherical shell of water or lye. Such systems are formed by surfactant/water systems which form spherical $L_1$ solutions in the absence of electrolyte. Most built liquid detergents in commercial use are of this spherulitic type.

II. A lamellar system, which may be associated with a second (higher electrolyte) conductivity trough, as a weak three dimensional reticular structure interspersed with lye. It is typically more viscous than the corresponding spherulitic system at comparable surfactant concentrations. Because of the relatively high viscosity these reticular lamellar systems have had more limited application.

Now discovered are detergent and toiletry formulations that provide stable, homogeneous pourable compositions at eg, surfactant concentrations in the range 20 to 70%, or higher, certain of which are capable of suspending solids such as builders and/or cosmetic, toiletry or pharmaceutical ingredients and which typically can be diluted without gel formation.

BRIEF DESCRIPTION

In particular are discovered certain such formulations which are stable, opaque spherulitic, or translucent G-phase compositions at surfactant concentrations of the order of 40 to 60% based on the total weight of surfactant and water, and which can be diluted, without forming immobile intermediate phases, to form stable clear, isotropic solutions at concentrations in the range 20 to 30% and down to wash liquor concentrations (eg. 0.01 to 0.1% surfactant).

It is also discovered that when sufficient dissolved electrolyte is added to hexagonal phases or to cubic (VI) phases a substantially Newtonian, mobile and substantially optically isotropic liquid, is frequently formed. The latter normally exhibits at least one distinctive peak in its X-ray or neutron diffraction plot. These solutions are apparently Newtonian, and usually clear, resembling unstructured micellar solutions in appearance.

However, the distinctive peaks which are usually in the 2 to 10 nm region are consistent with the presence of a hexagonal or lamellar structure, typically with a repeat spacing between 4.5 and 6.5 nm.

The compositions may possibly represent a microdispersed mesophase structure or a micellar system with prolate (rod shaped) micelles.

It is believed that the evidence is consistent with a prolate or oblate micellar system or with a dispersion of small, e.g. possibly less than 0.1 micron, domains of M-phase and/or G-phase.

The novel, clear phases of the invention are surprisingly mobile having regard to their high surfactant and substantial electrolyte content. On dilution they initially become more viscous, the viscosity passing through a maximum and then falling upon further dilution.

Further addition of electrolyte to the clear phases causes the d-spacing of the principal X-ray scattering peak to increase to a maximum and then fall sharply. As the d-spacing increases the composition becomes more clearly lamellar in character. The decline in d-spacing after the peak is accompanied by an increase in sharpness suggesting a more highly ordered system.

As the electrolyte level increases there is initially a sharp fall in viscosity accompanying the transition from the hexagonal or cubic phase to the clear phase. The viscosity then usually rises to a peak coinciding with the peak in d-spacing and then again falls sharply.

As the electrolyte content of the clear phase is increased, there is evidence of open bilayer structures dispersed in the clear liquid. Further additions of electrolyte may cause separation of an apparently lamellar phase, the proportion of which increases with the dissolved electrolyte concentration, and as the electrolyte level is increased still further, a first conductivity minimum is often observed, associated with the formation of a homogeneous, opalescent, apparently lamellar, composition which is believed to be a G-phase composition.

The latter is capable of providing a useful and novel washing or toiletry product. The formation of the G-phase and the conductivity minimum typically coincide with peaks in viscosity and d-spacing.

However the viscosity of the novel composition is substantially less than that normally associated with G-phases. Unlike conventional G-phases, which cannot be used, in practice, to suspend solids because the resulting suspensions are not pourable, the novel G-phase compositions of the invention can suspend substantial amounts of solid to form pourable suspensions, often with viscosities comparable to those of less concentrated spherulitic systems.

Further additions of electrolyte cause a relatively sharp transition to a stable, homogeneous, spherulitic phase associated with a conductivity trough, but typically at electrolyte concentrations less than that corresponding to the conductivity minimum, which is typically the second conductivity minimum.

The highly concentrated spherulitic composition and the homogeneous G-phase composition are mobile and capable of suspending solid particles such as solid builders or toiletry ingredients. They are also capable of dilution, usually without gel formation, to a clear, homogeneous, L-like solution.

It has been found that many of the surfactants which are preferred for toiletry use give novel structured systems according to the invention.

BRIEF DESCRIPTION OF THE DRAWINGS

(FIG. 4 is a contour plot which illustrates an alignment of scattering.)

DETAILED DESCRIPTION OF THE INVENTION

Figure 1:
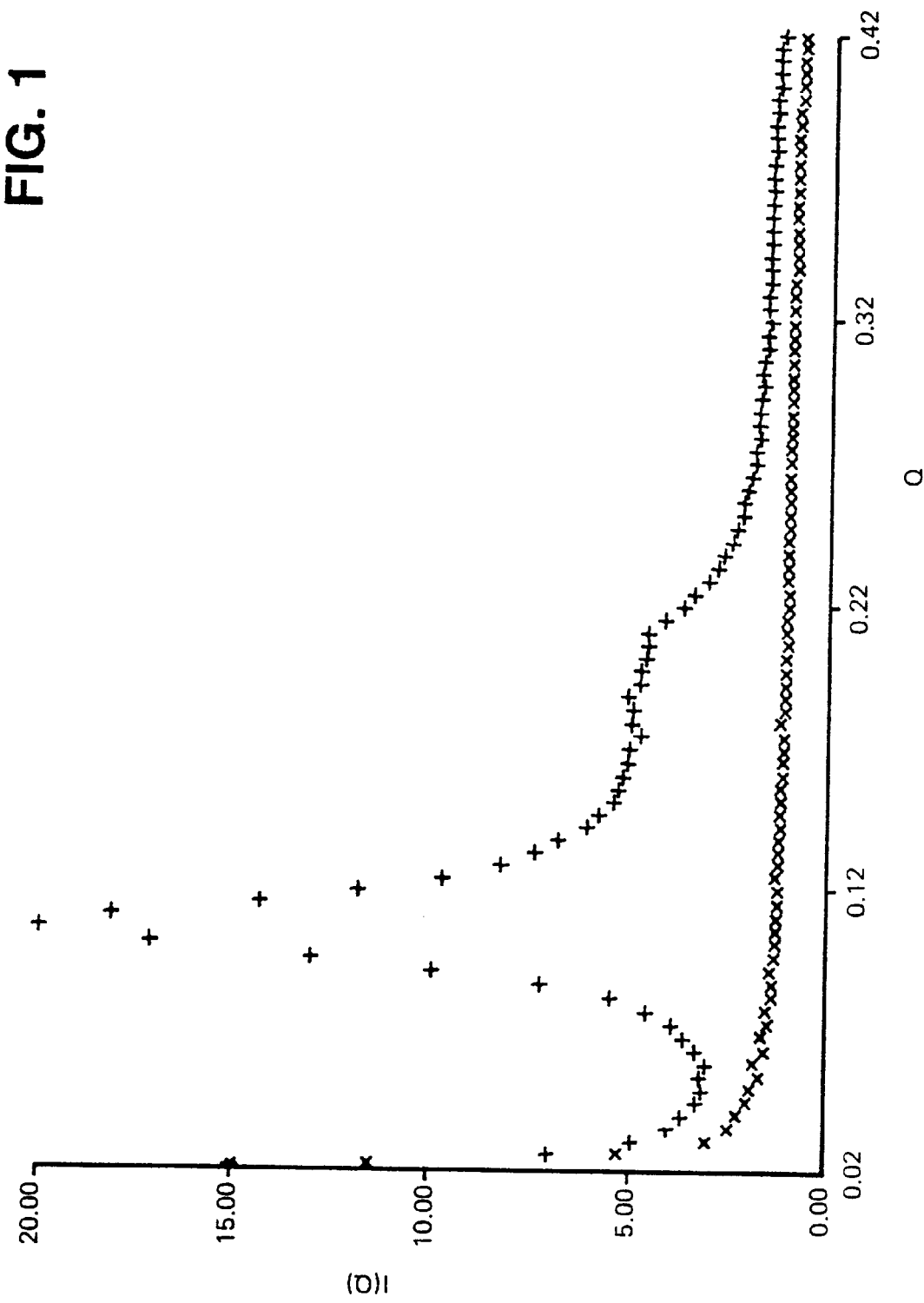
FIGS. 1–18 are plots of the X-ray diffraction spectra as set out in Table 7'.
Figure 2:
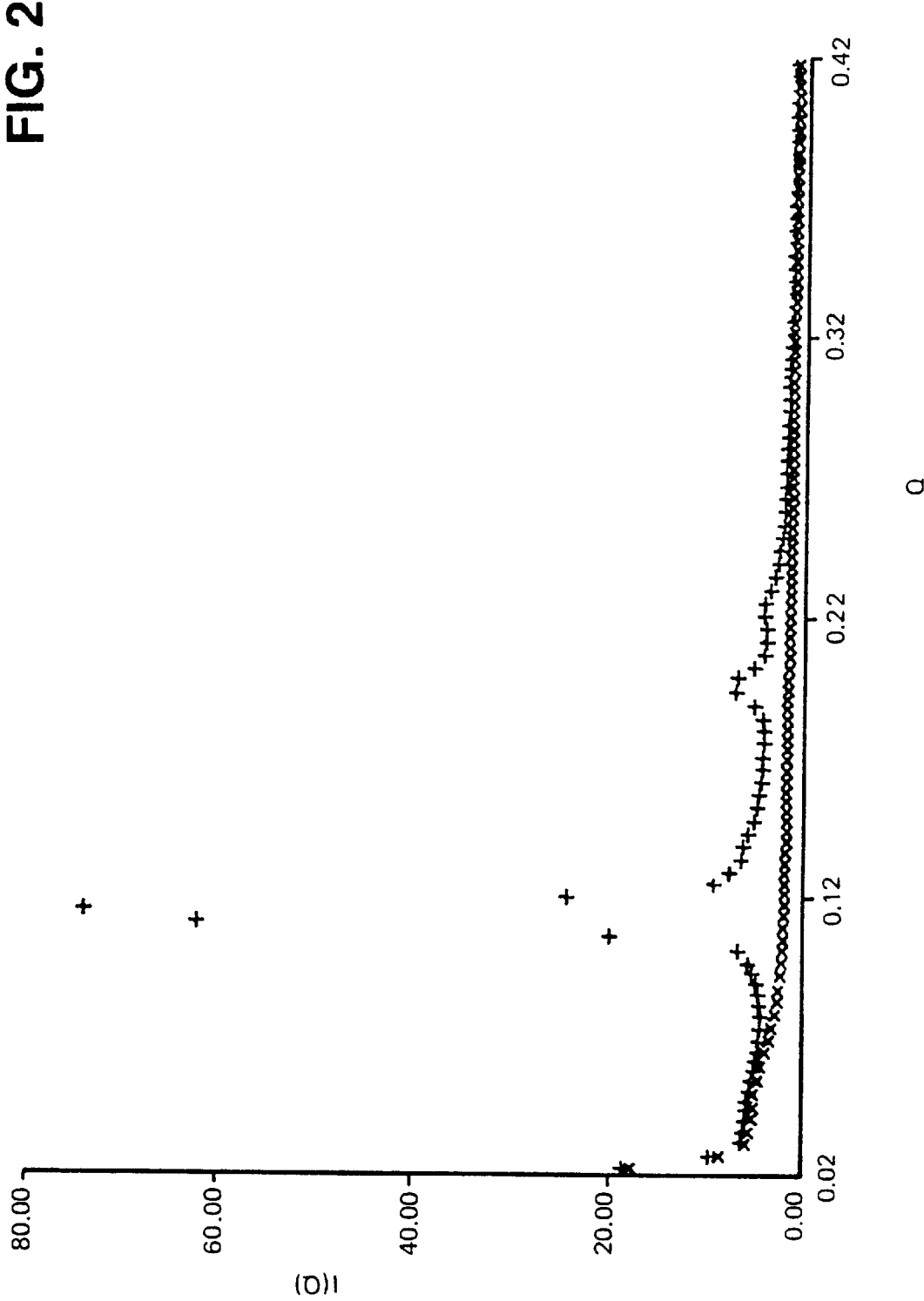
Figure 3:
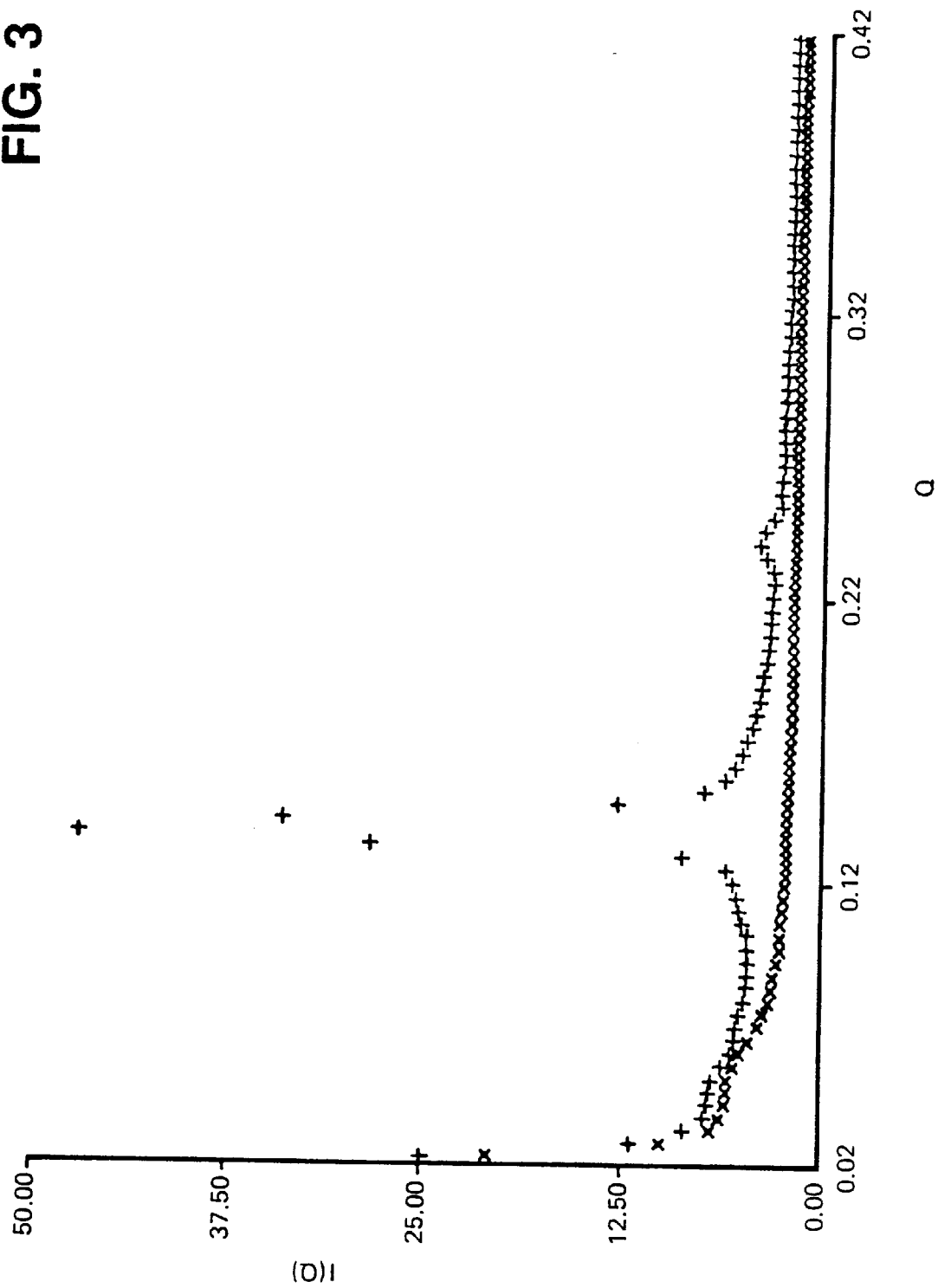

Without wishing to be limited by any theory, it is believed that the observations are consistent with the following explanation. When soluble electrolyte is added to a hexagonal or cubic phase, especially one formed by a surfactant mixture containing an appreciable proportion of a relatively soluble surfactant, the normally rigid or highly viscous phases characteristic of M or VI break down into short rod like structures (prolate micelles) which are sufficiently small to permit mobility but sufficiently crowded to exhibit a regular, ordered, hexagonal arrangement which is detectable by X-ray scattering but not by crossed polars.

When this clear prolate micellar phase is diluted, the spacing between the rods increases. Relieved of the constraint to adopt a highly ordered arrangement their orientation becomes more random giving a more "entangled" less ordered, and therefore more viscous system. On further dilution the micelles become progressively less prolate, and the system less viscous, as the system transforms into a conventional spherical micellar $L_1$-phase.

The addition of more electrolyte to the prolate micellar phase further breaks down the hexagonal or cubic symmetry to form an open (G-) composition which contains bilayers which are more widely separated than in conventional G-phases and which, with increasing electrolyte content, form spherulites. Throughout this process the total amount of surfactant salted out of solution is continually increasing as the electrolyte content increases.

The transition from open lamellar domains to spherulites is marked intially by an increase in the d-spacing indicating a greater (and less regular) separation between the shells of the spherulites than that between the lamellae of the G-phase, but further electrolyte causes the d-spacing to reduce as the bi-layers within the spherulites become more close packed. By the time that the spherulites are space filling, the surfactant is generally substantially all salted out and further additions of electrolyte, which tend to dehydrate the spherulites, merely reduce their diameter so that the system is no longer space filling.

The transition between the G-phase composition and the spherulitic composition may be effected by change of temperature, the former giving rise to the latter an cooling and the latter giving the former on heating.

By selecting water soluble builders such as sodium or potassium carbonate, silicate, pyrophosphate, citrate or nitrilotriacetate as the electrolyte it is possible to obtain high concentrations of both surfactant and builder in the same composition. Such compositions exhibit excellent washing properties, and can be formulated at viscosities similar to those of the more conventional solvent containing liquid detergents.

The spherulitic and lamellar compositions of the invention can, if desired accomodate insoluble or sparingly soluble solids, either builders such as sodium tripolyphosphate or zeolite, or other solids, such as pesticides, dyes, drilling mud solids, coal powder or abrasives or toiletry or pharmaceutical ingredients.

According to one embodiment, the invention provides a liquid detergent composition comprising: surfactant and water at a concentration which in the absence of electrolyte would form a pourable hexagonal or cubic phase; and sufficient dissolved surfactant-desolubilising electrolyte to form a substantially Newtonian and/or optically isotropic liquid composition.

According to a second embodiment, the invention provides a substantially Newtonian aqueous composition comprising at least 20% by weight of surfactant and at least 3% by weight of dissolved builder salt, said composition exhibiting a neutron scattering and/or X-ray diffraction peak between 4 and 10 nm and preferably having a viscosity which increases on dilution.

According to a third embodiment, the invention provides liquid detergent composition comprising water, from 25% to 75% preferably 30% to 75% especially 55% to 75% of total surfactant based on the total weight of surfactant and water and sufficient dissolved electrolyte to form a substantially Newtonian and/or optically isotropic liquid with a neutron scattering and/or x-ray diffraction peak between 4 and 10 nm, especially 4.5 to 8.5 nm preferably below 7 nm, e.g. 5.5 to 6.5 nm.

According to a fourth embodiment, the invention provides a pourable medium capable of suspending solids and comprising: a mixture of water and surfactant capable in the absence of electrolyte of forming a hexagonal or cubic phase or capable of providing a composition according to any foregoing embodiment; and sufficient dissolved surfactant-desolubiliser, e.g. a surfactant-desolubilising electrolyte, to provide a stable, spherulitic, or G-phase composition.

According to a fifth embodiment, the invention provides a liquid laundry detergent composition which comprises: water; surfactants, present in a concentration which is usually from 25 to 75% by weight, based an the total weight of surfactant and water, said surfactant at said concentration exhibiting a plot of electrical conductivity against dissolved electrolyte concentration with at least two conductivity troughs, comprising a first trough characterised by the formation of a lamellar phase and a second trough, corresponding to higher electrolyte concentrations than the first trough and being characterised by the formation of a turbid spherulitic phase; and an amount of dissolved, surfactant-desolubilising electrolyte corresponding to either of said first and second troughs and sufficient to form a stable, pourable, G-phase or spherulitic composition, respectively.

According to a sixth embodiment, the invention provides a liquid laundry detergent which comprises: water and at least 20%, by weight of the detergent, of surfactant, said surfactant being soluble in 5.5% aqueous potassium carbonate to form a clear optically isotropic liquid phase up to a concentration of at least 2% by weight surfactant and sufficient dissolved surfactant-desolubiliser to form a stable, spherulitic composition.

The present invention according to a further embodiment provides a structured surfactant composition capable of suspending solids and consisting essentially of water; surfactant in a concentration which, in the absence of electrolyte would form a hexagonal or cubic mesophase; and sufficient dissolved electrolyte to provide a concentration greater than that corresponding to the maximum in the plot of the d-spacing of the principal lamellar X-ray or neutron scattering peak against electrolyte concentration.

The surfactant systems which are useful according to the invention typically form an M-phase or pourable hexagonal phase and preferably have low cloud points at 20% concentration eg. below 0° C. preferably below −5° C. They typically exhibit a relatively high solubility, e.g. up to at least 15%, preferably at least 20%, in 5.5% potassium carbonate solution, before showinq signs of turbidity.

The surfactants are typically present in a total concentration corresponding to that at which they would form an M-phase, G-phase or pourable hexagonal phase in the absence of electrolyte, preferably from 30 to 75% based an the total weight of surfactant and water usually 35 to 70%, especially 40 to 70% based on the total weight of the composition, e.g. 50 to 60%.

The surfactants for use according to the invention are typically mixtures comprising a "soluble" surfactant, especially one that forms well defined M-phase or G-phase, and preferably both an M-phase and a G-phase such as an alkyl ether sulphate.

In order to obtain a stable spherulitic suspending medium, it is preferred that the surfactant additionally comprises a relatively "insoluble" surfactant, especially one that forms an $L_2$-phase, such as a non-ionic surfactant with relatively low HLB, and/or an anionic surfactant with a cloud point above 0° C., eg. sodium alkyl benzene sulphonate and/or a sodium soap.

According to an embodiment, the invention provides a pourable composition capable of suspending solids and comprising: a mixture of water and surfactant capable in the absence of dissolved surfactant-desolubiliser of forming a non-pourable liquid crystal phase and sufficient dissolved surfactant-desolubiliser, e.g. a surfactant-desolubilising electrolyte, to provide a stable spherulitic composition.

According to an embodiment, the invention provides a pourable composition comprising: a mixture of water and surfactant which in the absence of dissolved surfactant-desolubiliser would form a hexagonal or cubic phase; sufficient dissolved surfactant-desolubiliser to form a stable homogeneous G-phase composition; and a dispersed phase stably suspended therein.

According to an embodiment, the invention provides an aqueous composition which comprises: water; surfactant, present in a concentration (which is usually from 20 to 75% by weight, based on the total weight of surfactant and water) said surfactant at said concentration exhibiting a plot of electrical conductivity against dissolved surfactant-desolubiliser concentration with at least two conductivity minima, comprising a first minimum characterised by the formation of a G-phase composition and a subsequent minimum, corresponding to higher surfactant-desolubiliser concentrations than the first minimum and being characterised by the formation of a turbid spherulitic phase; and an amount of dissolved, surfactant-desolubiliser greater than that corresponding to said first minimum, but less than that corresponding to said subsequent minimum and sufficient to form a stable, pourable composition, capable of suspending solids.

According to an embodiment, the invention provides a liquid laundry detergent which comprises: water and at least 30%, by weight of the detergent, of surfactant, said surfactant being soluble in 5.5% aqueous potassium carbonate to form a clear optically isotropic liquid phase up to a concentration of at least 5% by weight surfactant and sufficient dissolved surfactant-desolubiliser to form a stable, spherulitic composition.

According to an embodiment, the invention provides (i) a mixture of water and surfactant, which on addition of dissolved surfactant-desolubiliser forms a G-phase and/or spherulitic composition associated with a principal X-ray diffraction peak corresponding to a d-spacing lying between 4 and 15 nm. which d-spacing increases to a maximum as the concentration of surfactant desolubiliser is increased, and then decreases, and which mixture has an electrical conductivity which passes through at least two conductivity minima as the concentration of surfactant-desolubiliser is increased, at least one of said conductivity minima occurring at a lower concentration than that corresponding to the d-spacing maximum and at least one conductivity minimum occurring at a concentration greater than said d-spacing maximum; and (ii) dissolved surfactant desolubiliser in a concentration corresponding to the conductivity trough containing the conductivity minimum next preceding the d-spacing maximum.

According to an embodiment, the invention provides a pourable composition comprising: (i) a mixture of water and surfactant adapted, on addition of a dissolved surfactant-desolubiliser to form a G-phase composition having at least one X-ray diffraction peak with a d-spacing between 4 and 15 nm, said d-spacing increasing with concentration of dissolved surfactant-desolubiliser to a d-spacing maximum and then falling, and said mixture having an electrical conductivity which, on addition or dissolved surfactant-desolubiliser passes through a minimum value, said minimum being located between two conductivity maxima which define a conductivity trough over a range of concentrations which includes that corresponding to said d-spacing maximum; and (ii) a dissolved surfactant-desolubiliser at a concentration, within said range, sufficient to provide a stable, homogeneous composition.

According to an embodiment, the invention provides a pourable composition comprising: (i) a mixture of water and surfactant adapted, on addition of a dissolved surfactant-desolubiliser, to form a G-phase composition having at least one X-ray diffraction peak corresponding to a d-spacing between 4 and 15 nm, said d-spacing increasing with increasing concentration of dissolved surfactant-desolubiliser to a d-spacing maximum and then falling, and said mixture having an electrical conductivity which, on addition of dissolved surfactant desolubiliser passes through a conductivity minimum at a concentration greater than that corresponding to said d-spacing maximum; and (ii) dissolved surfactant-desolubiliser at a concentration greater than that corresponding to said d-spacing maximum but less than that corresponding to said conductivity minimum.

The present invention according to an embodiment provides a structured surfactant composition capable of suspending solids and containing: water; surfactant in a concentration at which, in the absence of dissolved surfactant-desolubiliser said surfactant would form a hexagonal or cubic mesophase; and dissolved surfactant-desolubiliser in a concentration corresponding to the trough in the plot of dissolved surfactant-desolubiliser in said water and surfactant which trough includes the concentration corresponding to the maximum value in the plot of d-spacing of the principal lamellar X-ray diffraction or neutron scattering peak between 4 and 13 nm against the concentration of dissolved surfactant-desolubiliser in said water and surfactant; said dissolved surfactant-desolubiliser concentration being sufficient to provide a stable G-phase composition.

According to an embodiment, the invention provides a structured surfactant composition capable of suspending solids and containing: water; surfactant in a concentration at which, in the absence of surfactant-desolubiliser said surfactant would form a hexagonal or cubic mesophase; and dissolved surfactant-desolubiliser in a concentration greater than that corresponding to the maximum value in the plot of the d-spacing of the principal lamellar X-ray diffraction or neutron scattering peak between 4 and 13 nm against the concentration of dissolved surfactant-desolubiliser in said water and surfactant, and sufficient to provide a stable, spherulitic composition.

According to an embodiment, the invention provides a pourable composition comprising: (i) a stable translucent suspending medium comprising water, surfactant and dissolved surfactant-desolubiliser, exhibiting an X-ray diffraction peak corresponding to a d-spacing of from 7 to 15 nm, and (ii) a dispersed phase stably suspended in said medium. Additional embodiments of the invention include:

A liquid detergent composition consisting essentially of: water; surfactant in a concentration which would in the absence of electrolyte form a pourable hexagonal, or cubic phase at 20° C.; and sufficient dissolved electrolyte to form a substantially Newtonian liquid.

A liquid detergent composition consisting essentially of: water; surfactant in a concentration which would in the absence of electrolyte form an optically anisotropic pourable hexagonal phase at 20° C.; and sufficient dissolved electrolyte to form a substantially optically isotropic liquid.

A substantially Newtonian aqueous composition consisting essentially of at least 20% by weight surfactant and at least 3% by weight of dissolved builder salt, said composition exhibiting a neutron scattering or X-ray diffraction peak between 4 and 10 nm.

A liquid detergent composition consisting essentially of water, from 25% to 75% by weight of surfactant based on the total weight of the surfactant and water and sufficient dissolved electrolyte to form a substantially Newtonian liquid with an X-ray or neutron scattering peak between 5.5 and 6.5 nm.

A liquid detergent composition consisting essentially of water, from 25% to 75% by weight of surfactant, based on the total weight of surfactant and water and sufficient dissolved electrolyte to form an optically isotropic liquid with a neutron scattering or X-ray diffraction peak between 5.5 and 6.5 nm.

A liquid detergent composition consisting essentially of: water; from 5% to 9% by weight of alkyl ether sulphate; from 3% to 8% by weight of surfactants selected from alkyl benzene sulphonate and alkyl sulphate; from 0% to 5% by weight of soap; from 0% to 3% by weight of ethoxylated alcohol non-ionic surfactant; and from 2% to 8% by weight of sodium and or potassium carbonate, said detergent composition having a viscosity which rises on dilution with water to a maximum and then falls with further dilution.

A liquid detergent composition according to any one of the above wherein said surfactant consists essentially of from 20 to 75% by weight, based on the total weight of surfactants of a sodium $C_{10-20}$ alkyl 2 to 10 mol ethoxy sulphate, from 2 to 40% by weight based on the total weight of surfactant of a $C_{9-18}$ alcohol 2 to 20 mol ethoxylate and the balance consisting of at least one member selected from sodium alkylbenzene sulphonate and ethanolamine soaps.

A pourable composition capable of suspending solids and comprising: a mixture of water and surfactant which in the absence of surfactant-desolubiliser would form a non-pourable liquid crystal phase; and sufficient dissolved surfactant-desolubiliser to provide a stable spherulitic composition.

A pourable medium capable of suspending solids and consisting essentially of: a mixture of water and surfactant which in the absence of electrolyte would form (i) an immobile or pourable hexagonal, or (ii) a cubic, phase; and sufficient dissolved surfactant-desolubiliser to provide a stable spherulitic composition.

A liquid medium, capable of suspending solids which consists essentially of: a mixture of water and surfactant at a concentration at which the plot of electrical conductivity against concentration of dissolved surfactant-desolubilising electrolyte in said water and surfactant at said concentration exhibits at least two conductivity troughs, comprising a first trough which is characterised by the formation of a lamellar-phase and a second trough at higher electrolyte concentration than said first trough and characterised by the formation of a turbid spherulitic composition; and a quantity of dissolved surfactant desolubilising electrolyte corresponding to one of said troughs and sufficient to form a stable composition capable of suspending solid.

A pourable composition which comprises: a mixture of water and surfactant at a concentration at which the plot of electrical conductivity against concentration of dissolved surfactant-desolubiliser in said water and surfactant at said concentration exhibits at least two conductivity minima, comprising a first minimum which is characterised by the formation of a G-phase composition and a subsequent minimum at higher surfactant-desolubiliser concentration than said first minimum and characterised by the formation of a turbid spherulitic composition; and a quantity of dissolved surfactant-desolubiliser greater than that corresponding to said first minimum but less than that corresponding to said subsequent minimum and sufficient to form a stable composition capable of suspending solid.

A liquid laundry detergent consisting essentially of: water; at least 30% by weight of surfactant based on the total weight of said detergent, said surfactant being soluble in 5.5% aqueous potassium carbonate to form a clear optically isotropic liquid phase up to a concentration of at least 5% by weight; and sufficient dissolved surfactant-desolubiliser to form a stable spherulitic composition.

A structured surfactant composition capable of suspending solids and consisting essentially of: water; surfactant in a concentration at which, in the absence of electrolyte; said surfactant would form a hexagonal or cubic mesophase; and electrolyte said composition exhibiting a principal lamellar X-ray diffraction or neutron scattering peak corresponding to a d-spacing between 4 and 9 nm said d-spacing increasing with increasing concentration of dissolved electrolyte to a d-space maximum and then falling; and said electrolyte being present in a concentration greater than that corresponding to the maximum value in the plot of the d-spacing of said principal lamellar X-ray diffraction or neutron scattering peak against the concentration of dissolved electrolyte in said composition, and sufficient to provide a stable, spherulitic composition.

A structured surfactant composition capable of suspending solids and consisting essentially of: water; surfactant in a concentration at which, in the absence of dissolved surfactant-desolubiliser said surfactant would form a hexagonal or cubic mesophase; and dissolved surfactant-desolubiliser; said composition exhibiting a principal lamellar X-ray diffraction or neutron scattering peak corresponding to a d-spacing between and 13 nm said d-spacing increasing with increasing concentration of dissolved surfactant desolubiliser to a d-space maximum and then falling; and said surfactant-desolubiliser being present in a concentration greater than that corresponding to the maximum value in the plot of the d-spacing said principal lamellar X-ray diffraction or neutron scattering peak against the concentration of dissolved surfactant-desolubiliser in said water and surfactant, and sufficient to provide a stable, spherulitic composition.

A pourable composition comprising: (i) a mixture of water and surfactant adapted, on addition of a dissolved surfactant-desolubiliser, to form a G-phase composition having at least one X-ray diffraction peak corresponding to a d-spacing between 4 and 15 nm, said d-spacing increasing with increasing concentration of dissolved surfactant-desolubiliser to a d-space maximum and then falling, and said mixture having an electrical conductivity which, on addition of dissolved surfactant-desolubiliser passes through a conductivity minimum at a concentration greater than that corresponding to said d-space maximum; and (ii) dissolved surfactant-desolubiliser at a concentration greater than that corresponding to said d-space maximum but less than that corresponding to said conductivity minimum.

A pourable composition comprising: a mixture of water and surfactant which in the absence of surfactant-desolubiliser would form (i) a hexagonal, or (ii) a cubic phase; sufficient dissolved surfactant-desolubiliser to provide a stable, G-phase composition; and a dispersed phase stably suspended therein.

A pourable medium capable of suspending solids and consisting essentially of: a mixture of water and surfactant which in the absence of electrolyte would form (i) a pourable hexagonal, or (ii) a cubic phase; and sufficient dissolved surfactant-desolubiliser to provide a stable, G-phase composition.

A pourable composition containing:
(i) a mixture of water and surfactant, which on addition of dissolved surfactant-desolubiliser forms a G-phase and/or spherulitic composition associated with a principal X-ray diffraction peak corresponding to a d-space lying between 4 and 15 nm, which d-space increases to a maximum as the concentration of surfactant desolubiliser is increased, and then decreases, and which mixture has an electrical conductivity which passes through at least two conductivity minima as the concentration of surfactant-desolubiliser is increased, at least one of said conductivity minima occurring at a lower concentration than that corresponding to the d-space maximum and at least one conductivity minimum occurring at a concentration greater than said d-space maximum; and
(ii) dissolved surfactant desolubiliser in a concentration corresponding to the conductivity trough containing the conductivity minimum next preceding the d-space maximum.

A pourable composition containing:
(i) a mixture of water and surfactant, which on addition of dissolved surfactant-desolubiliser forms a G-phase and/or spherulitic composition associated with a principal X-ray diffraction peak corresponding to a d-space lying between 4 and 15 nm, which d-space increases to a maximum as the concentration of surfactant desolubiliser is increased, and then decreases, and which mixture has an electrical conductivity which passes through at least two conductivity minima as the concentration of surfactant-desolubiliser is increased, at least one of said conductivity minima occurring at a lower concentration than that corresponding to the d-space maximum and at least one conductivity minimum occurring at a concentration greater than said d-space maximum; and
(ii) dissolved surfactant desolubiliser in a concentration greater than that corresponding to the conductivity minimum next preceding said d-space maximum and less than that corresponding to the next subsequent conductivity minimum.

A pourable composition comprising:
(i) a mixture of water and surfactant adapted, on addition of a dissolved surfactant-desolubiliser to form a G-phase composition having at least one X-ray diffraction peak with a d-spacing between 4 and 15 nm, said d-spacing increasing with concentration of dissolved surfactant-desolubiliser to a d-space maximum and then falling, and said mixture having an electrical conductivity which, on addition of dissolved surfactant-desolubiliser passes through a minimum value, said minimum being located between two conductivity maxima which define a conductivity trough over a range of concentrations which includes that corresponding to said d-space maximum; and
(ii) a dissolved surfactant-desolubiliser at a concentration, within said range, sufficient to provide a stable, homogeneous composition.

A structured surfactant composition capable of suspending solids and comprising: water; surfactant in a concentration at which, in the absence of dissolved surfactant-desolubiliser said surfactant would form a hexagonal or cubic mesophase, and dissolved surfactant-desolubiliser in a concentration corresponding to the trough in the plot of conductivity against concentration of dissolved surfactant-desolubiliser in said water and surfactant which trough includes the concentration corresponding to the maximum value in the plot of d-spacing of the principal lamellar X-ray diffraction or neutron scattering peak between 4 and 13 nm against the concentration of dissolved surfactant-desolubiliser in said water and surfactant; said dissolved surfactant-desolubiliser concentration being sufficient to provide a stable G-phase composition.

A pourable composition comprising: (i) a stable translucent suspending medium comprising water, surfactant and dissolved surfactant-desolubiliser, exhibiting an X-ray diffraction peak corresponding to a d-spacing of from 7 to 15 nm; and (ii) a dispersed phase stably suspended in said medium.

A liquid detergent composition consisting essentially of water, from 10% to 15% by weight of sodium alkyl ether sulphate, from 4% to 10% by weight of surfactants selected from the group consisting of sodium alkyl benzene sulphonate and sodium alkyl sulphate, from 0% to 6% by weight soap, from 0% to 3% by weight ethoxylated non-ionic surfactant and from 8.5% to 12% by weight of sodium and/or potassium carbonate being a quantity sufficient to form a stable spherulitic composition.

The surfactant systems which are useful according to the invention typically form an M-phase or pourable hexagonal phase and preferably have low cloud points at 20% concentration eg. below 0° C. preferably below −5° C. They typically exhibit a relatively high solubility, e.g. up to at least 15%, preferably at least 20%, in 5.5% potassium carbonate solution, before showing signs of turbidity.

The surfactants are typically present in a total concentration corresponding to that at which they would form an M-phase, G-phase or pourable hexagonal phase in the absence of electrolyte, preferably from 30 to 75% based on the total weight of surfactant and water usually 35 to 70%, especially 40 to 70% based on the total weight of the composition, e.g. 50 to 60%.

The surfactants for use according to the invention are typically mixtures comprising a "soluble" surfactant, especially one that forms well defined M-phase or G-phase, or preferably both an M-phase and a G-phase, such as an alkyl ether sulphate.

In order to obtain a stable spherulitic suspending medium, it is preferred that the surfactant additionally comprises a relatively "insoluble" surfactant, especially one that forms an $L_2$-phase, such as a non-ionic surfactant with relatively low HLB, and/or an anionic surfactant with a cloud point above 0° C., eg. sodium alkyl benzene sulphonate and/or a sodium soap.

The term "solubility" is often used in relation to surfactant in a slightly different sense from its normal meaning. Many detergent surfactants are miscible with water in most proportions to form homogeneous compositions. Nevertheless some, such as alkyl ether sulphates, are commonly recognised as being more "soluble" than others such as sodium alkyl benzene sulphonates. Solubility may be recognised in terms of a low cloud point of an anionic surfactant or high inverse cloud point of a nonionic surfactant in a relatively concentrated eg, 20% $L_1$ solution; or in terms of high solubility in aqueous electrolyte.

The latter can be expressed either as the amount of surfactant which can be added to a given solution of electrolyte without causing turbidity or phase separation, or conversely the amount of electrolyte that can be added to an $L_1$ solution of surfactant at a given concentration without turbidity or phase separation. Unless the context requires otherwise, in this specification "Solubility" in relation to a surfactant means the amount of surfactant that can be dissolved in 5.5% potassium carbonate solution at 20° C. before turbidity is observed. Other criteria of a "soluble" surfactant include a high critical micellar concentration ie, the minimum concentration at which the surfactant forms micelles and below which it exists as a true solution, or a low Kraft point.

A further useful indication of solubility for the purposes of the invention is the effect of a small addition of electrolyte on the cloud point. The term "cloud point elevation" is used herein to refer to the difference between the cloud points of 20% by weight aqueous surfactant before and after addition of 1.3% w/w of sodium chloride.

It is preferred to use active systems which exhibit a cloud point elevation of less than 60° C., preferably less than 50° C. especially less than 40° C. desirably less than 30° C. particularly less than 20° C. It is preferred, in particular, systems in which the ratio of cloud point elevation to cloud point in °K ("the elevation ratio") is less than 0.22 preferably less than 0.18 more preferably less than 0.11 eg. 0.004 to 0.04.

It is preferred that at least a major proportion of the surfactant and preferably the total surfactant consists of surfactant having a solubility in 5.5% potassium carbonate of at least 5%, desirably at least 8%, especially at least 10% preferably at least 15% eg, at least 20%.

A 20% aqueous $L_1$ micellar solution of the more soluble surfactant for use according to the invention preferably has a cloud point below 0° C. especially below −2° C. most preferably below −5° C. According to one preferred embodiment the more soluble surfactant forms a well defined M-phase in binary mixtures with water.

The surfactant mixture preferably comprises at least 20% especially 20 to 75%, more preferably 25% to 50% most preferably 29% to 40%, of at least one relatively soluble surfactant based on the total weight of the surfactant. Typically it has been found that concentrations above about 8% of the more soluble surfactant, based on the total weight of the composition, are preferred, especially more than 10%, most preferably more than 12%. Preferably the soluble surfactant comprises anionic surfactants such as alkyl ether sulphates, alkyl ether carboxylates, triethanolamine soaps, potassium, ammonium or organic substitued ammonium, e.g. ethanolamine alkyl sulphates triethanolamine alkyl benzene sulphonates or sulphosuccinates. The soluble surfactant may additionally or alternatively comprise a non-ionic surfactant such as high HLB alcohol ethoxylate (eg, cetyl 20 mole ethoxylate) or an alkyl polyglycoside. Additionally or alternatively the soluble surfactant may comprise amine oxides or amphoteric surfactants such as imidazolines, betaines, or cationic surfactant such as dimethyl mono or bis-hydroxyethyl ammonium chloride.

The preferred soluble surfactant is alkyl ether sulphate which is preferably the product obtained by ethoxylating a natural fatty or synthetic $C_{10-20}$ e.g. a $C_{12-14}$ alcohol with from 1 to 20, preferably 2 to 10 e.g. 3 to 4 ethyleneoxy groups, optionally stripping any unreacted alcohol, reacting the ethoxylated product with a sulphating agent and neutralising the resulting alkyl ether sulphuric acid with a base. The term also includes alkyl glyceryl sulphates, and random or block copolymerised alkyl ethoxy/propoxy sulphates. The cation is typically sodium but may alternatively be potassium, lithium, calcium, magnesium, ammonium, or an alkyl ammonium having up to 6 aliphatic carbon atoms including monoethanolammonium, diethanolammonium, and triethanolammonium. Ammonium and ethanolammonium salts are generally more soluble than the sodium salts.

Thus sodium alkyl benzene sulphonates can be used as the less soluble components of the surfactant mixture whereas triethanolamine alkyl benzene sulphonates may constitute the more soluble component. In addition to, or instead of, the alkyl ether sulphate, the soluble component may comprise, for example, $C_{10-20}$ eg. $C_{12-18}$ especially $C_{14-18}$ olefin sulphonate or paraffin sulphonate or $C_{10-20}$ eg. $C_{12-18}$ ammonium or mono-, di- or tri-ethanolammonium alkyl sulphate, or a triethanolamine alkyl benzene sulphonate.

The surfactant may preferably comprise a $C_{8-20}$ eg. $C_{10-18}$ aliphatic soap. The soap may be saturated or unsaturated, straight or branched chain. Preferred examples include dodecanoates, myristates, stearates, oleates, linoleates, linolenates and palmitates and coconut and tallow fatty acids and their water soluble salts. The cation of the soaps may be sodium, or preferably potassium or mixed sodium and potassium, or alternatively any of the other cations discussed above in relation to the ether sulphates. Where foam control is a significant factor it is particularly preferred to include soaps e.g., ethanolamine soaps and especially triethanolamine soaps, which have been found to give particularly good cold storage and laundering properties, as part of the soluble component.

According to one embodiment, the soap and/or carboxylic acid is preferably present in a total weight proportion, based on the total weight of surfactant, of at least 20%, more preferably 20 to 75%, most preferably 25 to 50%, e.g. 29 to 40%.

The surfactant may include other anionic surfactants, such as taurides, isethionates, ether sulphonates, aliphatic ester sulphonates eg, alkyl glyceryl sulphonates, sulphosuccinates or sulphosuccinamates. Preferably the other anionic surfactants are present in total proportion of less than 45% by weight, based on the total weight of surfactants, more preferably less than 40% most preferably less than 30% e.g. less than 20%.

The surfactant preferably contains one or preferably more, non-ionic surfactants. These preferably comprise ethoxylated $C_{8-20}$ preferably $C_{12-18}$ alcohols, ethoxylated with 2 to 20 especially 2.5 to 15 ethyleneoxy groups. The alcohol may be fatty alcohol or synthetic e.g. branched chain alcohol. Preferably the non-ionic component has an HLB of from 6 to 16.5, especially from 7 to 16 e.g. from 8 to 15.5.

Mixtures of two or more non-ionic surfactants having a weighted mean HLB in accordance with the above values are particularly preferred.

Other ethoxylated non-ionic surfactants which may be present include $C_{6-16}$ alkylphenol ethoxylates, ethoxylated fatty acids, ethoxylated amines, ethoxylated alkanolamides and ethoxylated alkyl sorbitan and/or glyceryl esters.

Other non-ionic surfactants which may be present include amine oxides, fatty alkanolamides such as coconut monoethanolamide, and coconut diethanolamide, alkylpolyglycosides and alkylaminoethyl fructosides and glucosides.

The proportion by weight of non-ionic surfactant is preferably at least 2% and usually less than 40% more preferably less than 30% eg, 3 to 25% especially 5 to 20% based on the total weight of surfactant.

The surfactant may optionally comprise minor amounts of amphoteric and or cationic surfactants, for example betaines, imidazolines, amidoamines, quaternary ammonium surfactants and especially cationic fabric conditioners having two long chain alkyl groups, such as tallow groups.

The surfactant systems suitable for use in accordance with the invention typically form M-phases, G-phases, VI-phases or pourable hexagonal phases, in the absence of any dissolved surfactant-desolubiliser, which exhibit a sharp principal X-ray/neutron diffraction peak having a d-spacing between 4 and 6 nm together, usually, with higher order peaks at Q values $3^{0.5}$ and/or 2 times the Q value of the principal peak and sometimes (in the case of cubic phases) at $2^{0.5}$ of the Q value of the principal peak.

On addition of sufficient dissolved surfactant-desolubiliser, the aforesaid M- or pourable hexagonal phases usually provide a substantially clear solution. This may comprise rod shaped surfactant micelles, and/or a micro dispersed mesophase comprising small particles of M-phase, spherulites and/or G-phase, dispersed in an aqueous continuum. It may be a mobile, possibly Newtonian liquid. In the absence of non-surface active additives it is typically substantially clear or slightly hazy and shows no appreciable birefringence. It may be readily diluted with, or dispersed in, water, and does not form visible intermediate mesophases. The clear phase typically exhibits some small angle X-ray scattering, together with a distinct, fairly broad peak at between 4 and 7 nm. Typically the clear phase shows a slight increase in viscosity on dilution with small amounts of water. This may reflect a change in the shape and/or packing of the micelles or dispersed microparticles of mesophase, resulting in the particles becoming more randomly orientated.

Typically the clear phase has a viscosity of from 0.4 to 1.5 Pa.s, with a minimum viscosity at about 35 to 40% surfactant based on the total weight of surfactant and water.

In some cases hexagonal phases may form a mobile G-phase composition or a spherulitic phase according to our invention directly on addition of dissolved surfactant-desolubiliser, without forming an intermediate $L_1$ phase.

The surfactant-desolubiliser is preferably a surfactant-desolubilising electrolyte.

Where the clear phases of the invention are used as detergents, in addition to surfactants and electrolyte they preferably contain minor additives such as enzymes, dyes, perfume, opacifiers, antifoams, preservatives, anti-redeposition agents, optical brighteners, deodorisers, sanitisers, soluble bleach such as hydrogen peroxide and, where desired to improve viscosity, hydrotropes. Solvents are preferably absent or present in amounts less than 5% by weight e.g. less than 3% especially less than 2% most preferably less than 1%.

It is preferred that the electrolyte should comprise basic electrolytes such as sodium or potassium carbonates and/or silicates. These have the advantage of maintaining an alkaline pH in wash liquor, and of functioning as builders. Generally it is preferred that at least the major proportion, and preferably all, of the electrolyte comprises builder or other functional electrolyte.

Electrolytes which may be present include such builders as citrates, nitrilotriacetates, pyrophosphates and ethylene diamine tetracetates, as well as other salts such as chlorides, bromides, formates, acetates and nitrates or buffers such as borates.

For cost reasons, sodium salts are preferred where possible although it is generally desirable to include some potassium salts in the electrolyte to obtain lower viscosities. Lithium and cesium salts have also been tested successfully, but are unlikely to be used in commercial formulations.

It is possible to include phosphates and/or condensed phosphates, such as potassium pyrophosphate or sodium tripolyphosphate. Phosphonates, such as acetodiphosphonic acid salts or amino tris (methylenephosphonates), ethylene diamine tetrakis (methylenephosphonates) and diethylene triamine pentakis (methylenephosphonates), may also be used.

The electrolyte may be present in concentrations up to saturation, but it is preferred that any non-functional component not exceed its saturation concentration at 0° C. For this reason the electrolyte should preferably not contain substantial proportions e.g. more than 2% by weight of sodium sulphate. Preferably the sodium sulphate content is below 1% by weight. The total dissolved electrolyte concentration is typically between 2 and 20% by weight, more usually 4 to 18% eg. 6 to 17%, based on the total weight of the composition. In particular it is preferred that compositions of the invention should contain at least 2% preferably at least 3% more preferably at least 5% most preferably at least 6%, especially at least 7% sometimes at least 8% e.g. at least 9% by weight of dissolved builder.

The solid-suspending systems of the invention may for example have a structure substantially as described in EP 086614, EP 170091 and/or EP 151884 (Corresponding to U.S. Pat. No. 4,618,446 or U.S. Pat. No. 4,793,943). The compositions may be prepared and formulated substantially in accordance with the general teaching of the aforesaid Patents, but using the surfacants and surfactant concentrations as taught herein and, where appropriate, adjusting to the second rather than the first conductivity trough. In the latter case the concentration should usually be adjusted to a value less than that corresponding to the second conductivity minimum. For the purpose of this specification the trough comprises the part of the plot between successive maxima.

The solid-suspending systems of the invention may for example have a spherulitic structure, substantially as described in EP 151884 (Corresponding to U.S. Pat. No. 4,793,943) but typically associated with a second or subsequent conductivity minimum rather than with the first conductivity minimum. Alternatively the solid-suspending system may comprise a mobile G-phase composition. This is usually associated with a first conductivity minimum and/or with a d-space maximum.

Concentrations of electrolyte lying between that corresponding to the conductivity minimum next preceding the d-space maximum and the next subsequent conductivity minimum are particularly preferred.

This is accomplished in accordance with the general teaching of the aforesaid Patents, but using the surfacants and surfactant concentrations as taught herein and, where appropriate, adjusting to the second, or subsequent, rather than the first conductivity trough. In the latter case the concentration should usually be adjusted to a value less than that corresponding to the second conductivity minimum. For the purpose of this specification the trough comprises the part of the plot between succesive maxima.

Thus the conductivity of the composition may be measured, as electrolyte is progressively added. When turbidity is observed a series of formulations may be prepared with different concentrations of electrolyte within the conductivity troughs which correspond to the G-phase composition and/or the spherulitic phase and tested by centrifuging at 20,000 G in order to determine the optimum concentration for stability. Generally compositions approximately midway between the first and second conductivity minima, eg, corresponding to the conductivity maximum which separates said minima, are preferred.

Typically the suspending system is a mobile G-phase composition which is substantially less viscous than conventional G-phases and is characterised by an X-ray scattering peak indicating relatively wide d-spacing eg, greater than 7 nm more usually 7.5 to 14 nm especially 8 to 13 nm preferably 8.5 to 12 nm. The system is translucent, or even transparent in the absence of suspended solids, unlike the systems normally used in detergents.

The suspending system is capable of suspending particles of pesticides for agricultural or horticultural application, weighting agents for use as oilfield drilling muds, e.g. calcite or barite, pigments or disperse dyes for use in dyebaths or as printing pastes or optical brighteners for use in detergent manufacture.

The compositions of the invention may also find application as cutting fluids, lubricants, hydraulic fluids, heat transfer fluids or in similar functional fluids.

Examples of toiletry suspensions which have been successfully formulated according to the invention include shampoos, liquid soaps, creams, lotions, balms, ointments, antiseptics and styptics comprising suspensions of exfoliants such as talc, clays, polymer beads, sawdust, silica, seeds, ground nutshells and dicalcium phosphate, pearlisers such as mica or glycerol or ethylene glycol mono- or di-stearate, natural oils such as coconut, evening primrose, groundnut, meadow foam, apricot kernel, peach kernel, avocado and jojoba, synthetic oils such as silicone oils, vitamins, antidandruff agents such as zinc omadine (zinc pyrithione) and selenium disulphide, proteins, emollients such as lanolin, isopropyl myristate, glyceryl isostearate or propylene glycol distearate, waxes and sunscreens such as titanium dioxide or zinc oxide. Suspended oils may be suspended directly as dispersed droplets or may be encapsulated in a polymer such as gelatin to provide suspended pressure release microcapsules. Porous particles (so called microsponges) containing absorbed active ingredients may be suspended. Other active ingredients which may be suspended include insect repellants and topical pharmaceutical preparations, eg, preparations for treatment of acne, fungicides for athlete's foot or ringworm or antiseptics or antihistamines. Pigments, such as the iron oxides, may also be added.

Surfactant systems which are preferred for use in toiletry formulation include ether sulphates, ether carboxylates, alkyl polyglycosides, amphoteric surfactants such as imidazolines and betaines, amine oxides, sulphosuccinates and soaps. These surfactants which are preferred on account of such properties as skin mildness, foaming and/or wetting power generally contrast with the surfactant systems used in laundry detergents, which have typically, hitherto, been based on alkyl benzene sulphonates. It is preferred that toiletry formulations contain an ethoxylated alcohol especially a 1–4 mole ethoxylate of a $C_{10-20}$ alcohol and/or an alkyl isothionate.

It is preferable that the solid suspending systems contain particles of solid builders, to provide a fully built liquid detergent. The preferred builders are zeolite and sodium tripolyphosphate. The builder may be present in concentrations up to 40% by weight of the composition e.g. 15 to 30%. The amount of dissolved electrolyte required (including any dissolved portion of the builder) is typically between 8 and 20% e.g. 10 to 18% based on the total weight of the composition. The compositions may also contain inert abrasives for use as scouring creams.

The pH of the composition may be neutral or below for toiletry applications eg, 5.0 to 7.5 but for laundry use is preferably alkaline, as measured after dilution to 1% by weight of the formulation, e.g. 7 to 12, more preferably 8 to 12, most preferably 9 to 11.

Compositions of the invention may optionally contain small amounts of hydrotropes such as sodium xylene sulphonate, sodium toluene sulphonate or sodium cumene sulphonate, e.g in concentrations up to 5% by weight based on the total weight of the composition preferably not more than 2% e.g. 0.1 to 1%. Hydrotropes tend to break surfactant structure and it is therefore important not to use excessive amounts. They are primarily useful for lowering the viscosity of the formulation, but too much may render the formulation unstable.

Preferably, the detergent composition of the invention should have a high total payload of surfactant and builder. Preferably the payload is greater than 30% by weight, more preferably 40 to 80% eg, 45 to 75% most preferably over 50%.

The solid-suspending detergent compositions of the invention may comprise conventional detergent additives such as antiredeposition agents (typically sodium carboxymethyl cellulose or polymers such as polyacrylates), optical brighteners, sequestrants, antifoams, enzymes, enzyme stabilisers, preservatives, dyes, colourings, perfumes, fabric conditioners, eg. cationic fabric softeners or bentonite, opacifiers, or chemically compatible bleaches. It has been found that peroxygen bleaches, especially bleaches that have been protected e.g. by encapsulation, are more stable to decomposition in formulations according to the invention than in conventional liquid detergents. Generally all conventional detergent additives which are dispersible in the detergent composition as solid particles or liquid droplets, in excess of their solubility in the detergent, and which are not chemically reactive therewith may be suspended in the composition.

The compositions may contain solvents. However, like hydrotropes, solvents tend to break surfactant structure. Moreover, again like hydrotropes, they add to the cost of the formulation without substantially improving the washing performance. They are moreover undesirable on environmental grounds and the invention is of particular value in providing solvent-free compositions. It is therefore preferred that they contain less than 6%, more preferably less than 5%, most preferably less than 3%, especially less than 2%, more especially less than 1%, e.g. less than 0.5% by weight of solvents such as water miscible alcohols or glycols, based on the total weight of the composition. It is preferred that the composition should essentially solvent-free, although small amounts of glycerol and propylene glycol are sometimes desired in toiletry formulations.

Detergent compositions or suspending media of the invention may be prepared by obtaining the surfactant at the concentration in water at which it forms a pourable hexagonal, VI-, or M-phase and adding to it sufficient of the electrolyte to convert the hexagonal, or cubic phase into a suspending medium. However, it is preferable to avoid formation of the, usually, more viscous surfactant/water compositions by adding the electrolyte to the ether sulphate or other soluble surfactant, prior to mixing the latter with any less soluble surfactants.

It may sometimes be preferable to prepare the composition by adding an aqueous electrolyte of appropriate composition to a G-phase surfactant mixture.

The invention is illustrated by the following examples in which all proportions, unless stated to the contrary, are percentages by weight based on the total weight of the composition.

The following abreviations set out in Table 1 will be used in the ensuing tables.

TABLE 1

| | |
|---|---|
| LABS | is sodium $C_{10-14}$ linear alkyl benzene sulphonate; |
| KSN | is sodium $C_{12-18}$ alkyl three mole ethyleneoxy sulphate (mean mole weight 440); |
| KB2 | is $C_{12-14}$ natural alcohol 2 mole ethoxylate |
| ESB | is sodium $C_{12-14}$ alkyl 2 mole ethoxy sulphate (Mean Mole Weight 384) |
| TEA | is triethanolamine; |
| APG | is $C_{12-14}$ alkyl polyglucoside with an average degree of polymerisation of 1.3 |
| CAPB | is $C_{12-14}$ alkyl amido propyl betaine |
| DSLES | is disodium lauryl ethoxy sulphosuccinate |
| $TiO_2$ | is finely divided titanium oxide supplied as a 50% w/w dispersion under the Registered Trademark "Tioveil" AQ |
| Zn Py | is zinc pyrithione (supplied as 48% aqueous dispersion) |
| CBS/X | is a proprietary optical brightner sold under the Registered; Trademark "TINOPAL CBS/X"; |
| SXS | is sodium xylene sulphonate, 93% active; |
| 91-2.5 | is a $C_{9-11}$ alcohol with 2.5 moles average ethylene oxide; |
| 91-12 | is $C_{9-11}$ alcohol with twelve moles average ethylene oxides; |
| PKFA | is palm kernel fatty acid. |
| ESC 3 | is $C_{12-14}$ 3 mole ether sulphate |
| BB | is $C_{12-14}$ alkyl dimethyl betaine |
| LX | is $C_{12-14}$ sodium lauryl sulphate |
| S132 | is Silicone antifoam sold under the Registered Trademark WACKER S132 |
| KC3 | is $C_{12-18}$ 3 mole alcohol ethoxylate |

Briquest 543 is sodium diethylene triamine pentakis - (methylene phasphonate). BRIQUEST is a Registered Trademark
Praxel GXL is a proprietary preservative sold under the Registered Trademark PROXEL GXL

EXAMPLES 1–5

The formulations in the table II below were made up. The products were stable, homogeneous, opaque, mobile, spherulitic compositions. Into one sample of Example 1 was stirred 20% by weight of a zeolite detergent builder. The resulting composition was stable to storage at ambient temperature after three months.

Each of examples 1 to 4 was diluted by slowly adding an equal volume water with stirring. The compositions diluted readily, without any sign of gel formation to form clear aqueous solutions.

Example 5 was a stable opaque suspension, which did not sediment after 3 months at laboratory ambient temperature.

TABLE II

| EXAMPLE NO. | 1 | 2 | 3 | 4 | 5 |
|---|---|---|---|---|---|
| LABS | 3.0 | 3.0 | 3.02 | 3.02 | 2.5 |
| $C_{9/11}$ alkyl sulphate | 3.0 | 3.0 | 3.02 | 3.02 | 2.5 |
| KSN | 14.3 | 14.42 | 14.52 | 14.54 | 10.9 |
| 91-12 | 1.2 | 1.2 | 1.21 | 1.21 | 0.85 |

TABLE II-continued

| EXAMPLE NO. | 1 | 2 | 3 | 4 | 5 |
|---|---|---|---|---|---|
| 91-2.5 | 3.0 | 3.0 | 3.02 | 3.02 | 2.5 |
| PKFA | 3.0 | 3.0 | 3.02 | 3.02 | 2.5 |
| SXS | 0.6 | — | 0.61 | — | 0.5 |
| TEA | 1.8 | — | 1.82 | — | 1.3 |
| CBS/X | 0.1 | 0.1 | 0.1 | 0.1 | 0.2 |
| Perfume | 0.5 | 0.5 | 0.5 | 0.2 | 0.5 |
| Dye | 0.01 | 0.01 | 0.01 | 0.01 | — |
| Potassium carbonate | 10.6 | 9.82 | 7.67 | 7.66 | 9.0 |
| Potassium hydrogen carbonate | — | — | 5.56 | 5.55 | — |
| Formalin | 0.075 | 0.08 | 0.08 | 0.08 | 0.075 |
| Zeolite | — | — | — | — | 20.00 |
| Sodium chloride | — | — | — | — | 1.0 |
| Water | | | Balance | | |
| Viscosity *Pa · s | 0.64 | 1.12 | 0.96 | 0.88 | 1.0 |
| pH (0.2% w/waq.) | 10.00 | 9.76 | 9.5 | 9.6 | 10.8 |

*Measured on Brookfield RVT (Spindle 4) at speed setting 100.

EXAMPLE 6

A surfactant mixture was prepared comprising 1 part triethanolamine 1.27 parts $C_{12-18}$ 3 mole alcohol ethoxylate 1.36 parts Na $C_{10-14}$ linear alkyl benzene sulphonate 2.04 parts palm kernel fatty acid 2.17 parts Na $C_{12-18}$ alkyl 3 mole ethyleneoxy sulphate at a total active concentration of 30.3% w/w in deionised water. Potassium citrate monohydrate was then added to this mixture (keeping the surfactant to water ratio constant) to give a range of samples from zero to 26% electrolyte. The conductivity and viscosity of each sample was measured, this data is given in Table (III). X-ray data was also obtained on selected samples from this series and the d-spacing of the principal X-ray diffraction peak is given in nm.

TABLE III

| % Potassium Citrate Monohydrate | Conductance $mS\ cm^{-1}$ | Viscosity (Brookfield RVT Spindle 4 speed 100) Pa · s | d-spacing nm |
|---|---|---|---|
| 0 | 9.2 | 2.34 | 7.4 |
| 2 | 7.2 | 2.68 | 8.0 |
| 4 | 2.8 | 2.16 | 9.9 |
| 6 | 2.4 | 2.68 | 10.1 |
| 8 | 2.8 | 2.24 | 10.4 |
| 10 | 3.6 | 1.2 | 10.8 |
| 12 | 3.7 | 1.0 | 11.0 |
| 14 | 4.2 | 1.1 | 11.0 |
| 16 | 4.2 | 1.44 | 11.5 |
| 15 | 4.3 | 2.24 | 10.0 |
| 20 | 2.8 | 2.20 | 6.9 |
| 21 | 6.2 | 1.64 | 6.0 |
| 22 | 10.5 | 0.52 | 5.7 |
| 24 | 22 | 0.32 | 5.1 |
| 26 | 26 | 0.32 | 4.8 |

The electrical conductivity of the solution fell to a minimum as electrolyte content increased, the minimum coinciding approximately with the first stable sample. The X-ray trace suggested an atypical lamellar phase with a large d-spacing. Electron microscopy and optical microscopy supported this view. The product was translucent and resembled a G-phase in appearance but was substantially more mobile than a conventional G-phase. On addition of more electrolyte the conductivity rose to a maximum and then fell, the maximum coinciding approximately to the maximum d-spacing. At the same time the composition became turbid. The turbid compositions were clearly spherulitic under both electron and optical microscopy. Further addition of electrolyte caused the conductivity to fall to a second minimum, whereupon the turbid compositions were unstable and separated into two layers.

EXAMPLE 7

An aqueous composition was prepared comprising:

| | |
|---|---|
| KSN | 10.4 |
| PKFA | 13.8 |
| TEA | 6.8 |
| LABS | 10.4 |
| Sodium Citrate dihydrate | 10.4 |
| Potassium Carbonate | 4.0 |

The composition was a stable, mobile, translucent, lamellar, liquid crystal detergent. It had good washing properties and was readily dilutable without gel formation. The composition was capable of suspending zeolite builder. A sample was mixed with 20% by weight of zeolite and provided a stable, pourable cream which showed no sign of separation over three months storage at ambient temperature.

Examples 8 to 11 were prepared by mixing the ingredients as shown in % by weight an weight with the balance in each case water, and adjusting the pH to 6.5–7.0 with citric acid. In each case perfume was added subsequently.

EXAMPLE 8

A shampoo base was prepared as follows:

| | |
|---|---|
| APG | 10% |
| KB2 | 10% |
| ZnPy | 5% solids |
| Potassium Citrate | 9% |

The product was a stable pourable suspension having a viscosity (measured on a Brookfield RVT viscometer, spindle 4 at 100 rpm) of 0.87 Pas. Progressive addition of potassium citrate to the aqueous surfactants (10% APG and 10% $KB_2$) in increments of 1% had indicated two conductivity minima, the first at 6%, and the second above 10% the latter being associated with a turbid spherulitic composition. The actual citrate was selected to lie between the two minima, and corresponded approximately to the peak at 9%.

EXAMPLE 9

A facial cleaning composition base was prepared as follows:

| | |
|---|---|
| ESB | 7.5% |
| KB2 | 7.5% |
| Polymer beads | 10.0% |
| Potassium citrate | 5.0% |

The product was a stable pourable suspension having a viscosity (measured an a Brookfield RVT viscometer spindle 4 at 100 rpm) of 1.46 Pas.

When potassium citrate was added in increments of 10% to the aqueous surfactants (7.5% ESB and 7.5% KB2) the conductivity passed through minima at 4 and 6%.

EXAMPLE 10

A shampoo base was prepared as follows:

| | |
|---|---|
| ESB | 7.5% |
| KB2 | 7.5% |
| Coconut oil | 5.0% |
| Potassium citrate | 5.0% |

The product was a stable, pourable suspension having a viscosity (measured an a Brookfield RVT viscometer spindle 4 at 100 rpm) of 1.62 Pas.

EXAMPLE 11

A Sunscreen composition was prepared as follows:

| | |
|---|---|
| DSLES | 8.0% |
| KB2 | 12.0% |
| $TiO_2$ | 10.0% solids |
| Potassium citrate | 6.0% |

The product was a stable, pourable suspension having a viscosity (measured on a Brookfield RVT viscometer, spindle 4 at 100 rpm) of 1.14 Pas.

When potassium citrate was added to, the aqueous surfactant (8% DSLES and 12% KB2) in increments of 1%, the conductivity rose to a maximum at around 1%, fell to a minimum at around 2%, rose to a second maximum at around 5% and fell to a second minimum between 6 and 7%. The compositions containing 2%, 3%, 4%, 5% and 6% citrate were stable and homogeneous. Those between 2% and 5% were translucent G-phase compositions. The composition of the example was an opaque packed spherulitic system, lying between the second conductivity maximum and the second conductivity minimum and exhibiting a strong X-ray diffraction peak at 12.5 nm. This was close to the d-space maximum.

EXAMPLE 12

A facial wash was prepared as follows:

| | |
|---|---|
| ESB | 6.5% |
| KB2 | 6.5% |
| CAPB | 2.0% |
| Avacado Oil | 5.0% |
| Potassium citrate | 5.0% |

The product was a stable, pourable suspension having a viscosity (measured on a Brookfield RVT viscometer, spindle 4 at 100 rpm) of 0.61 Pas.

EXAMPLES 13 to 16

TABLE IV

| Example No | 13 | 14 | 15 | 16 |
|---|---|---|---|---|
| Calcium acetate | 0.1 | 0.15 | 0.1 | 0.1 |
| CBS/X | 0.15 | 0.1 | 0.15 | 0.15 |
| ESC 3 | 5.1 | 6.0 | — | 5.1 |
| Zeolite | 28.0 | 25.0 | 25.0 | 21.5 |
| S132 | 0.2 | 0.2 | 0.2 | 0.2 |
| Treithanolamine | 2.35 | — | 2.2 | 2.3 |
| Potassium Carbonate | — | 1.0 | 4.0 | 2.0 |
| Sodium Carbonate | 1.0 | — | — | — |

TABLE IV-continued

| Example No | 13 | 14 | 15 | 16 |
|---|---|---|---|---|
| PKFA | 2.65 | — | 4.5 | 4.8 |
| BB | 0.6 | — | — | — |
| KC3 | 4.0 | 3.25 | 4.0 | 3.0 |
| Potassium Citrate Monohydrate | 10.25 | — | — | 13.75 |
| LX | — | 2.0 | — | — |
| Briquest 543 | — | 0.75 | 0.7 | 0.75 |
| Sodium Citrate dihydrate | — | 10.0 | 11.0 | — |
| SXS | — | — | 0.5 | — |
| KSN | — | — | 4.8 | — |
| LABS | — | 6.6 | 3.0 | 3.2 |
| Proxel GXL | 0.05 | 0.05 | 0.05 | 0.05 |
| Perfume | 0.45 | 0.45 | 0.5 | 0.45 |
| Protease Enzyme | 0.4 | 0.4 | 0.4 | 0.4 |
| Amylase Enzyme | 0.2 | 0.2 | — | — |
| Water | | BALANCE | | |
| Viscosity 20° C. 21 S$^{-1}$ (cp) | 1300 | 1520 | 1480 | 1340 |
| Conductance ° C. m Scm$^{-1}$ | 8.6 | 7.0 | 6.2 | 10.2 |

The formulations in the table above were prepared. The products were stable, homogeneous, opaque compositions having a surfactant structure corresponding to the region between the two conductivity minima as hereinbefore defined.

The invention is further illustrated by the following examples, wherein as in the above examples, all proportions, unless stated to the contrary, are percentages by weight based an the total weight of the composition. The compositions set out in the following tables 2', 3' and 4', other than example 20', which is comparative, were all mobile liquids with excellent washing performance. The balance in each case was water.

Figure 4:
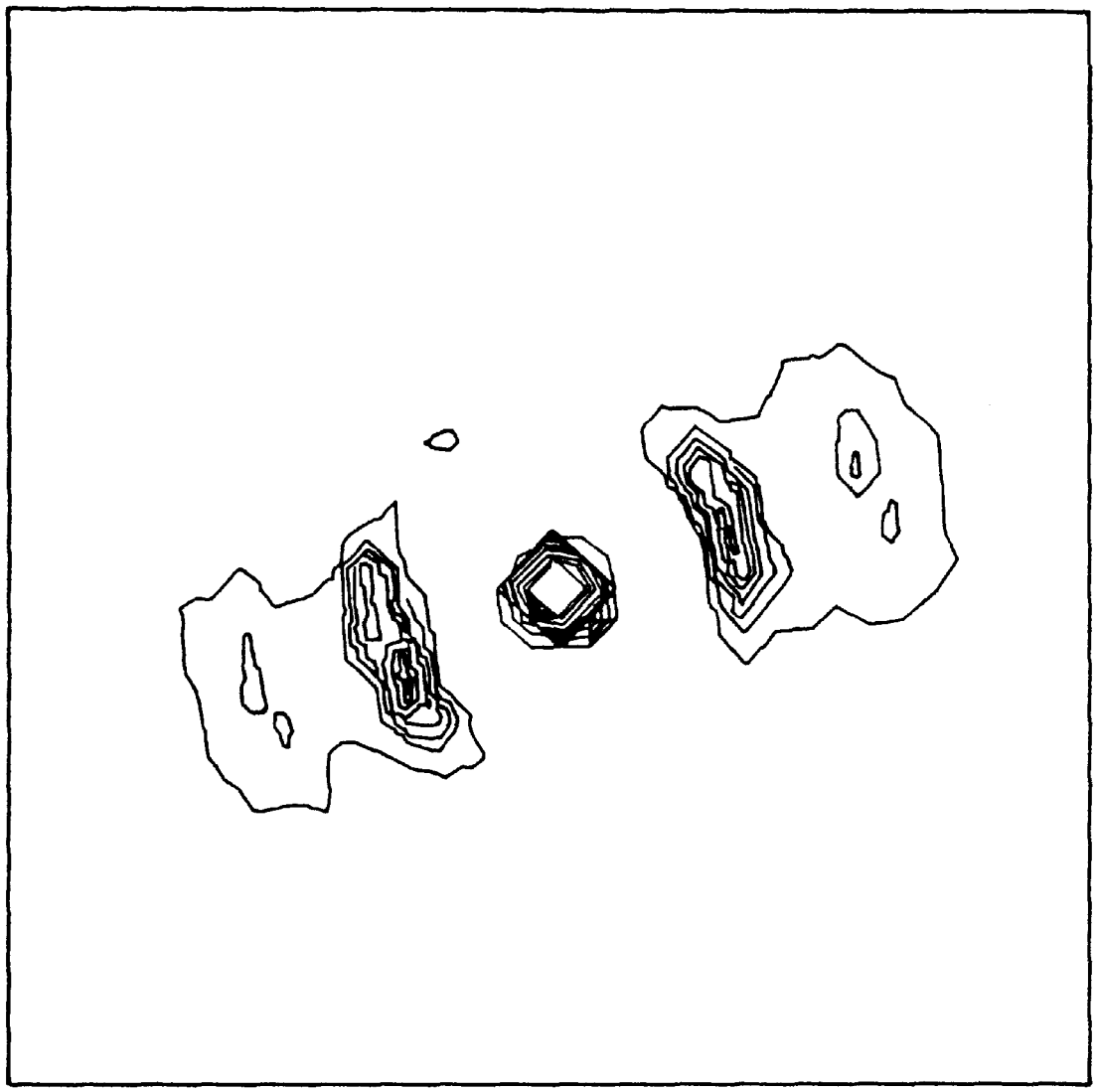
Figure 5:
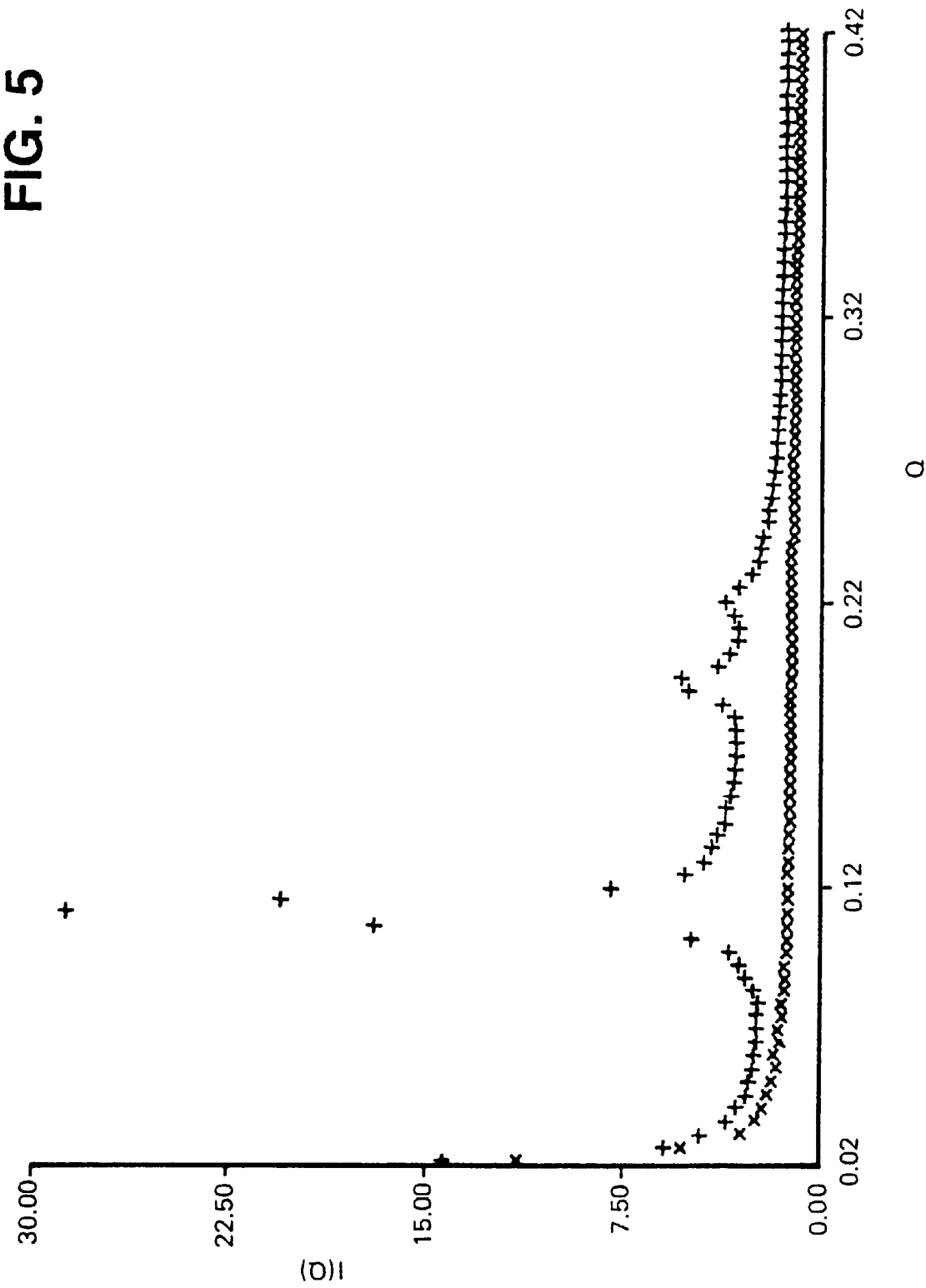
Figure 6:
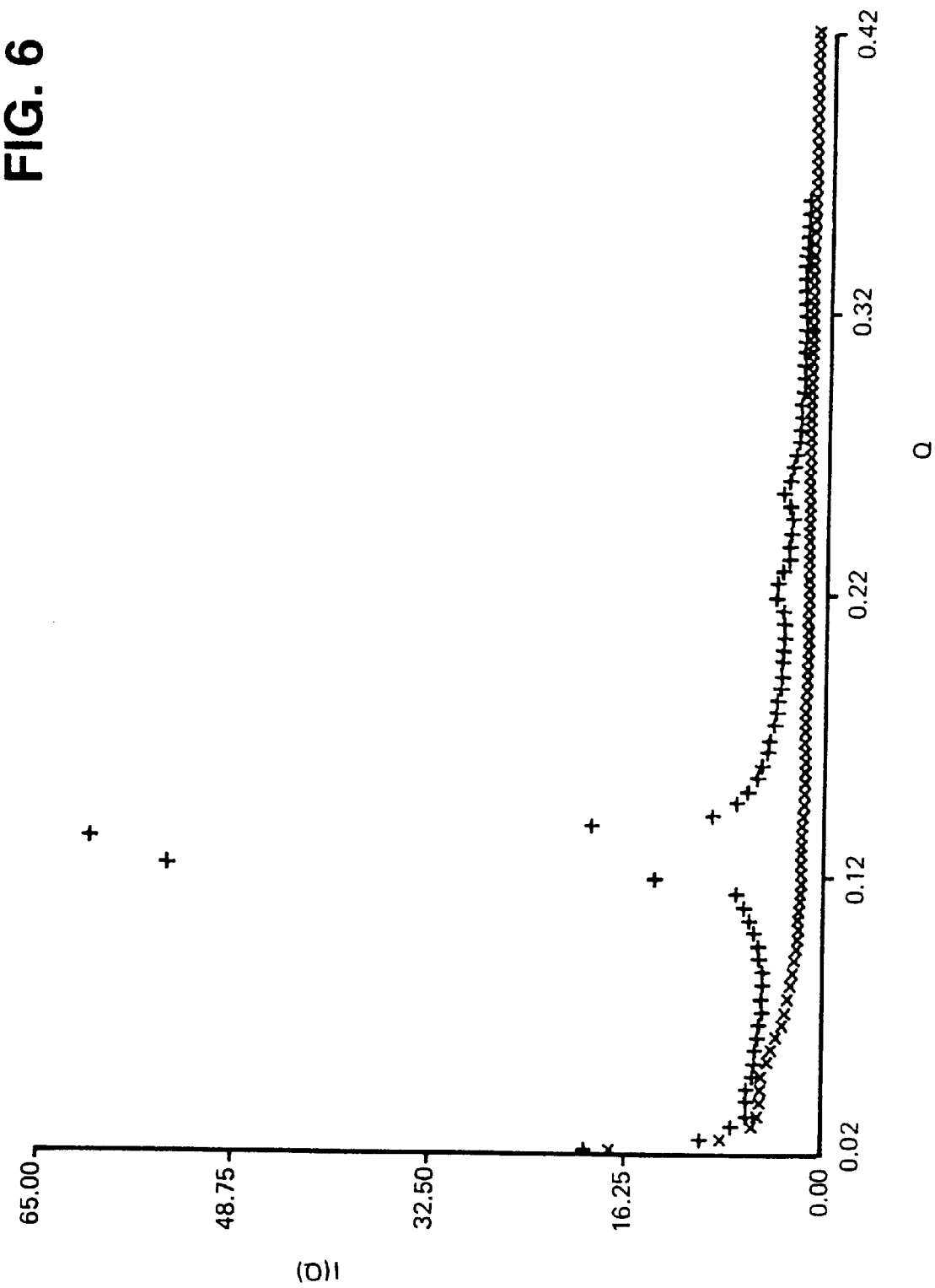
Figure 7:
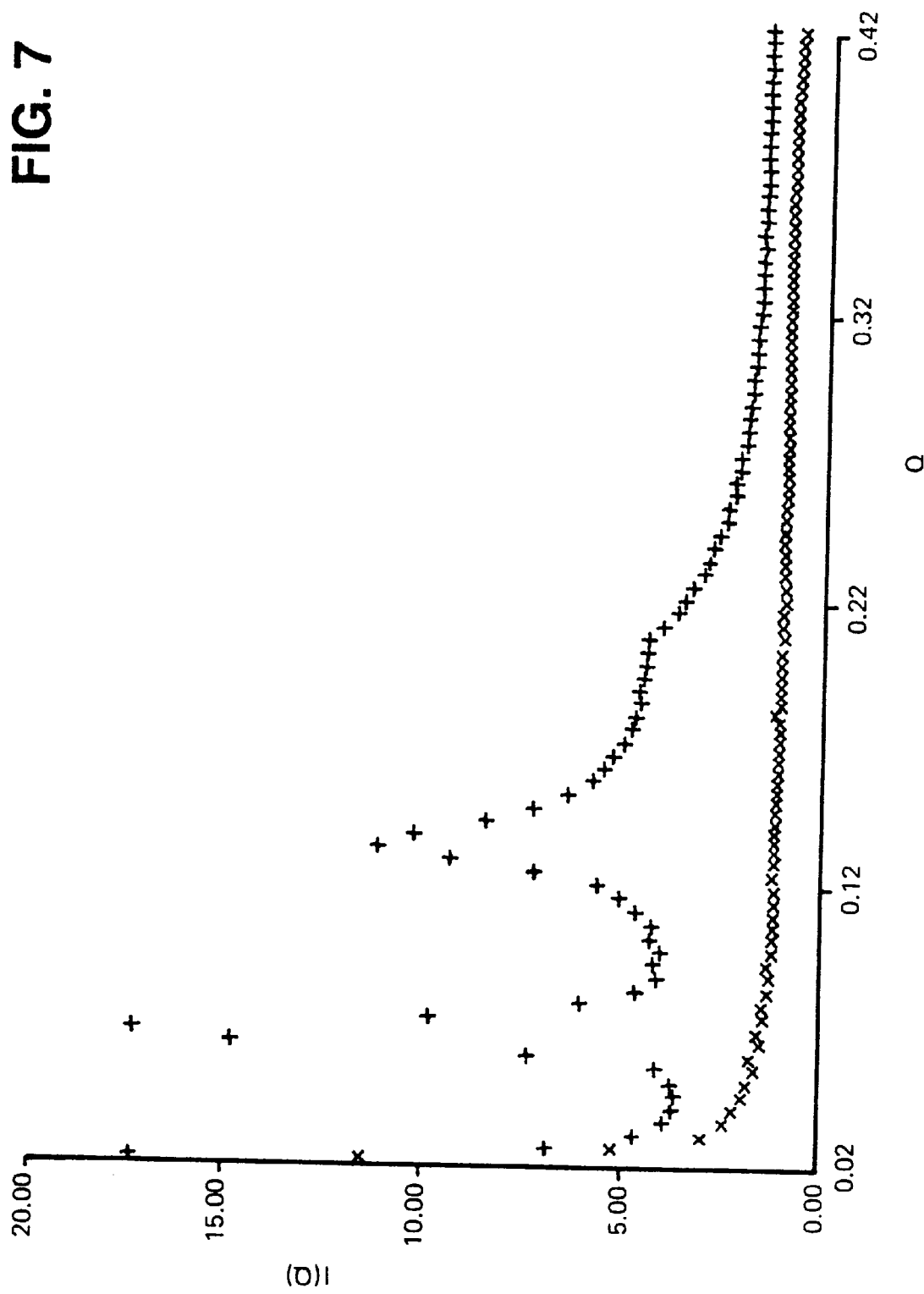
Figure 8:
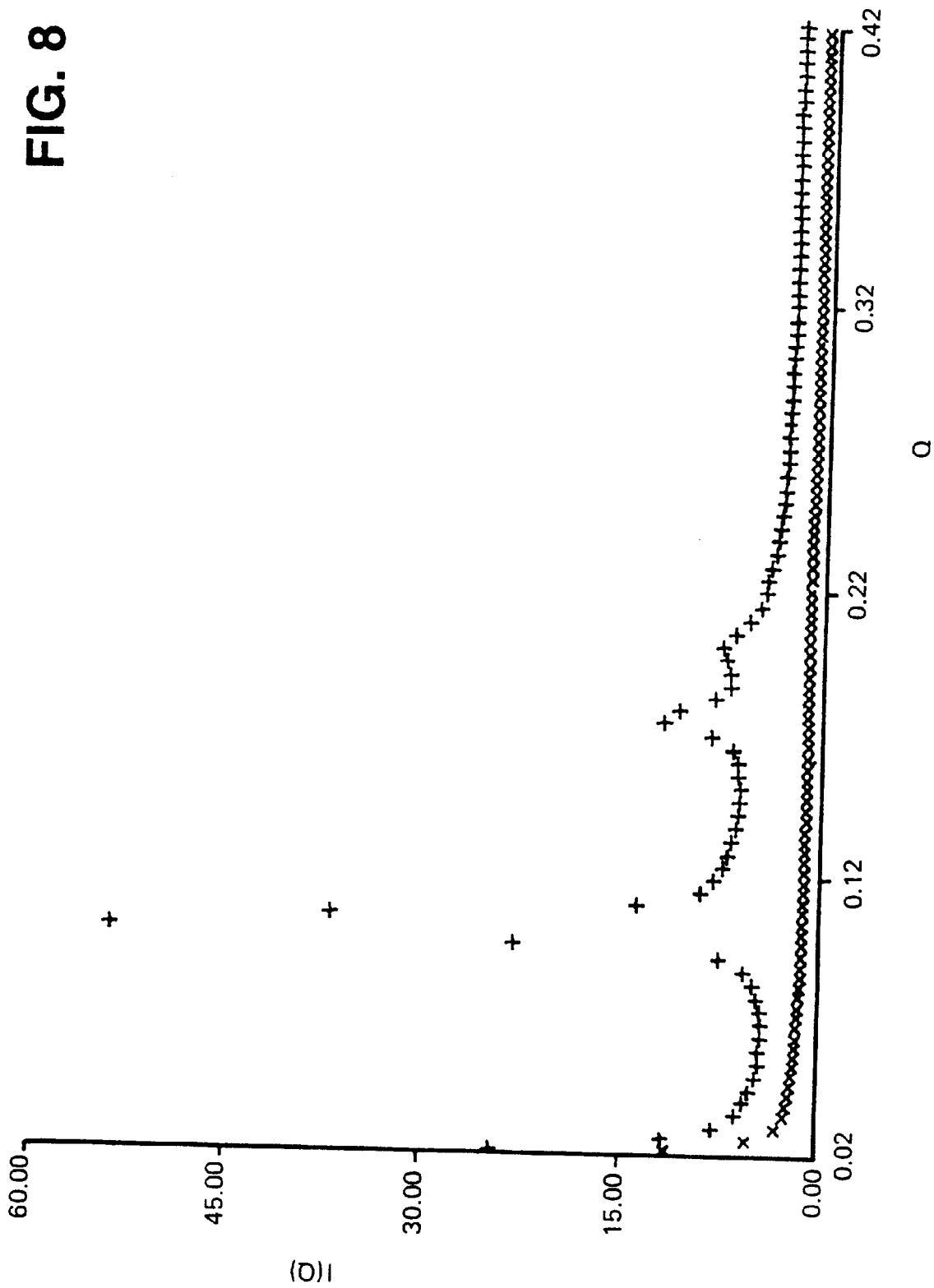
Figure 9:
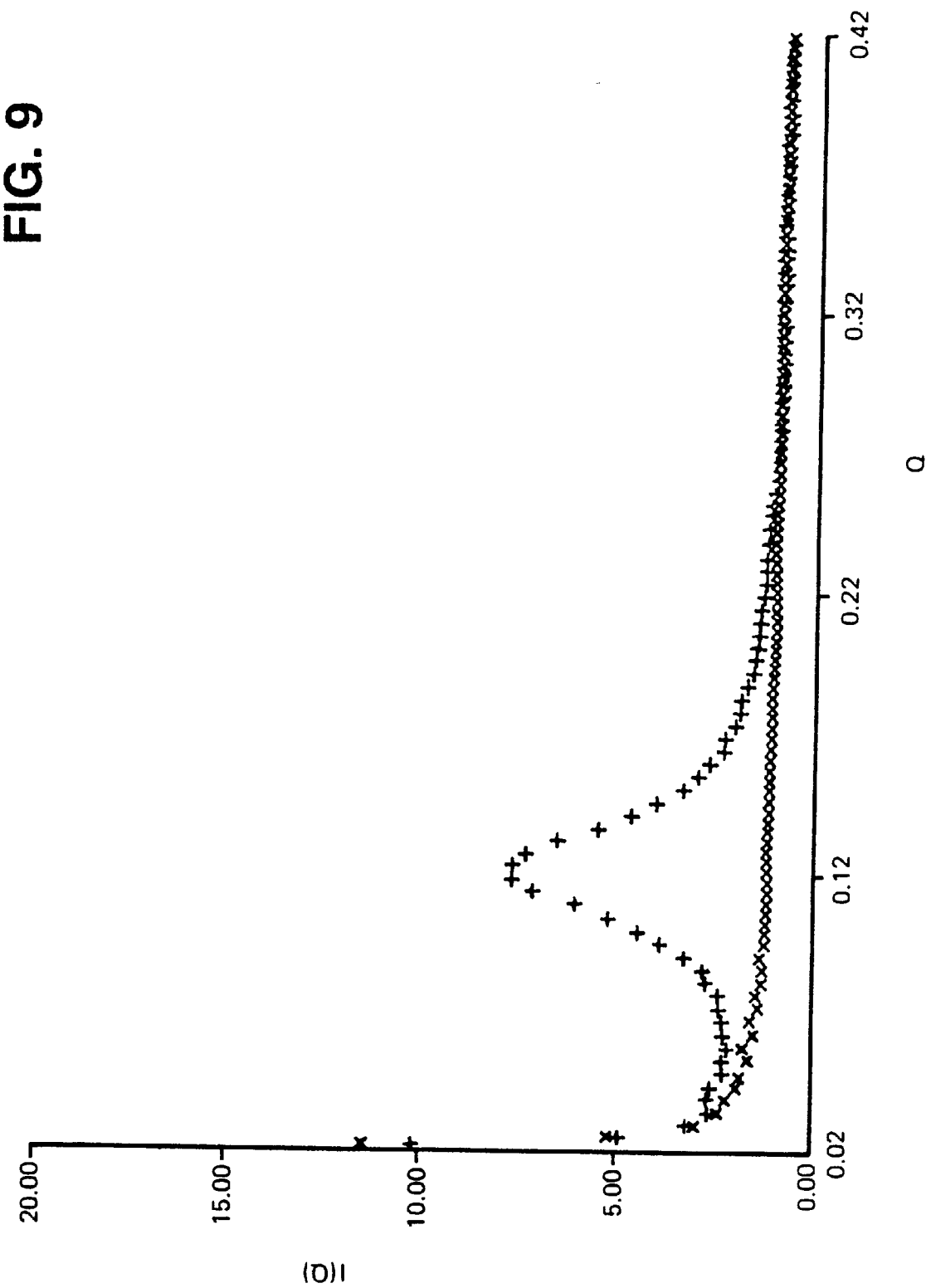
Figure 10:
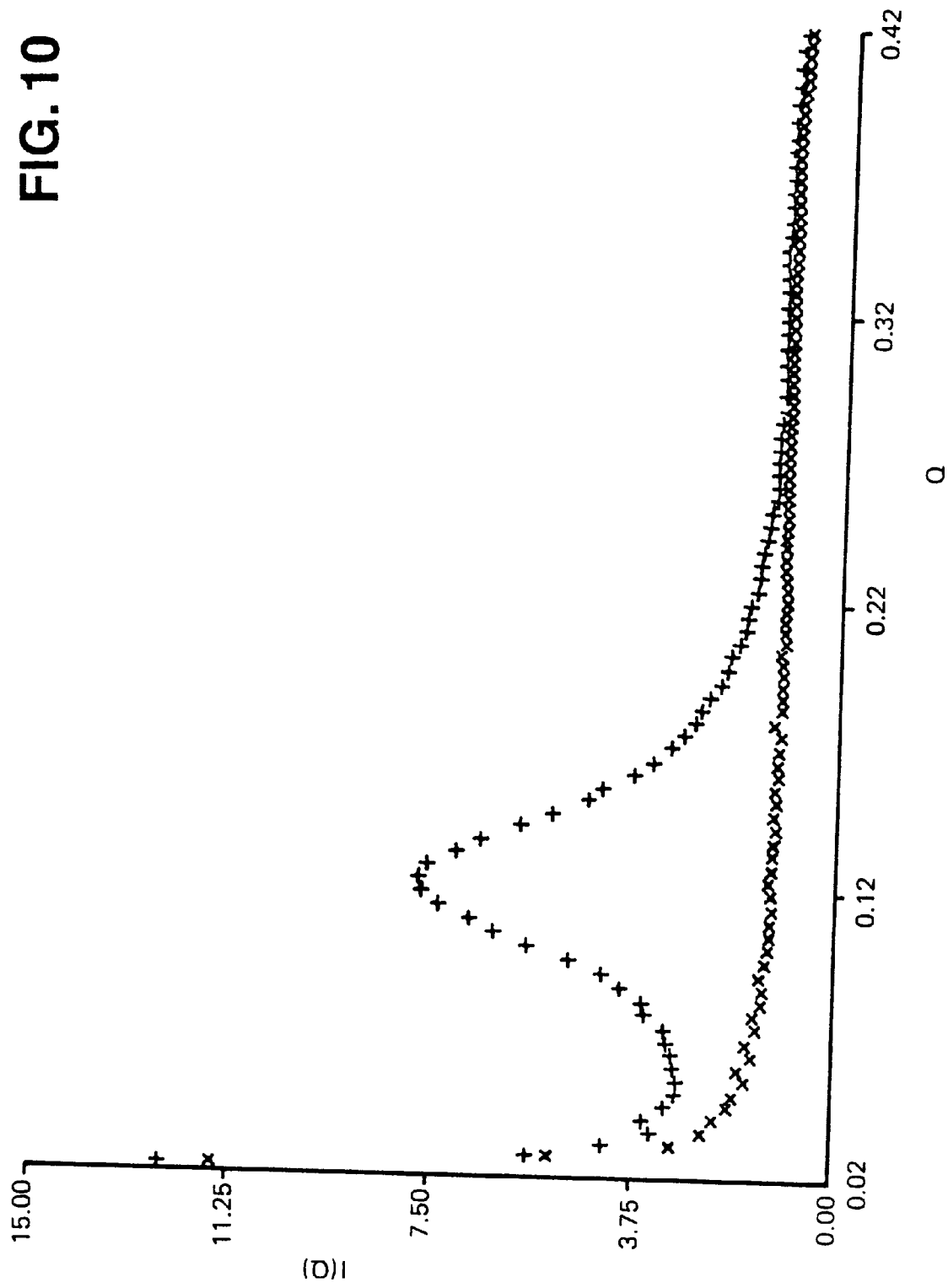
Figure 11:
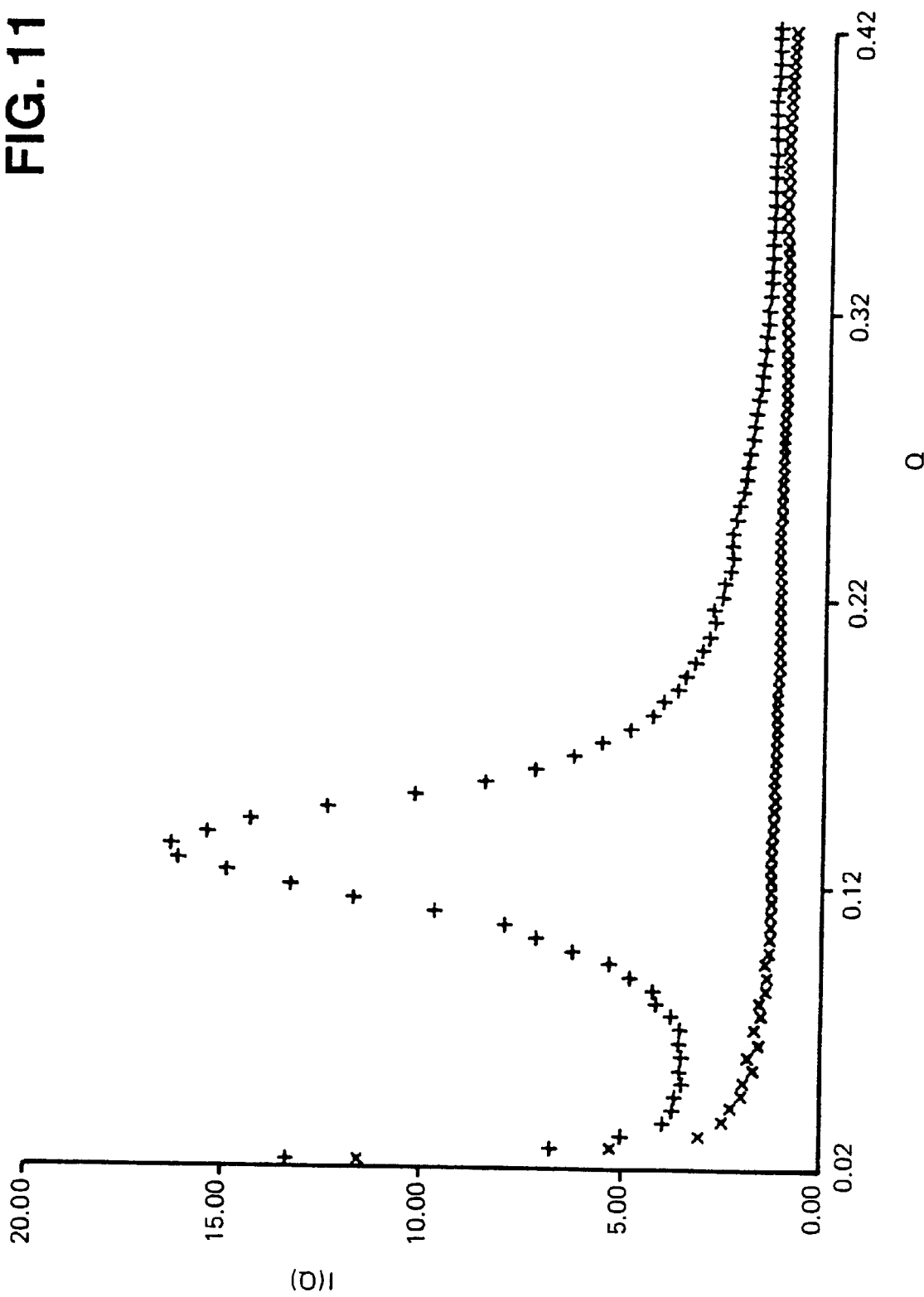
Figure 12:
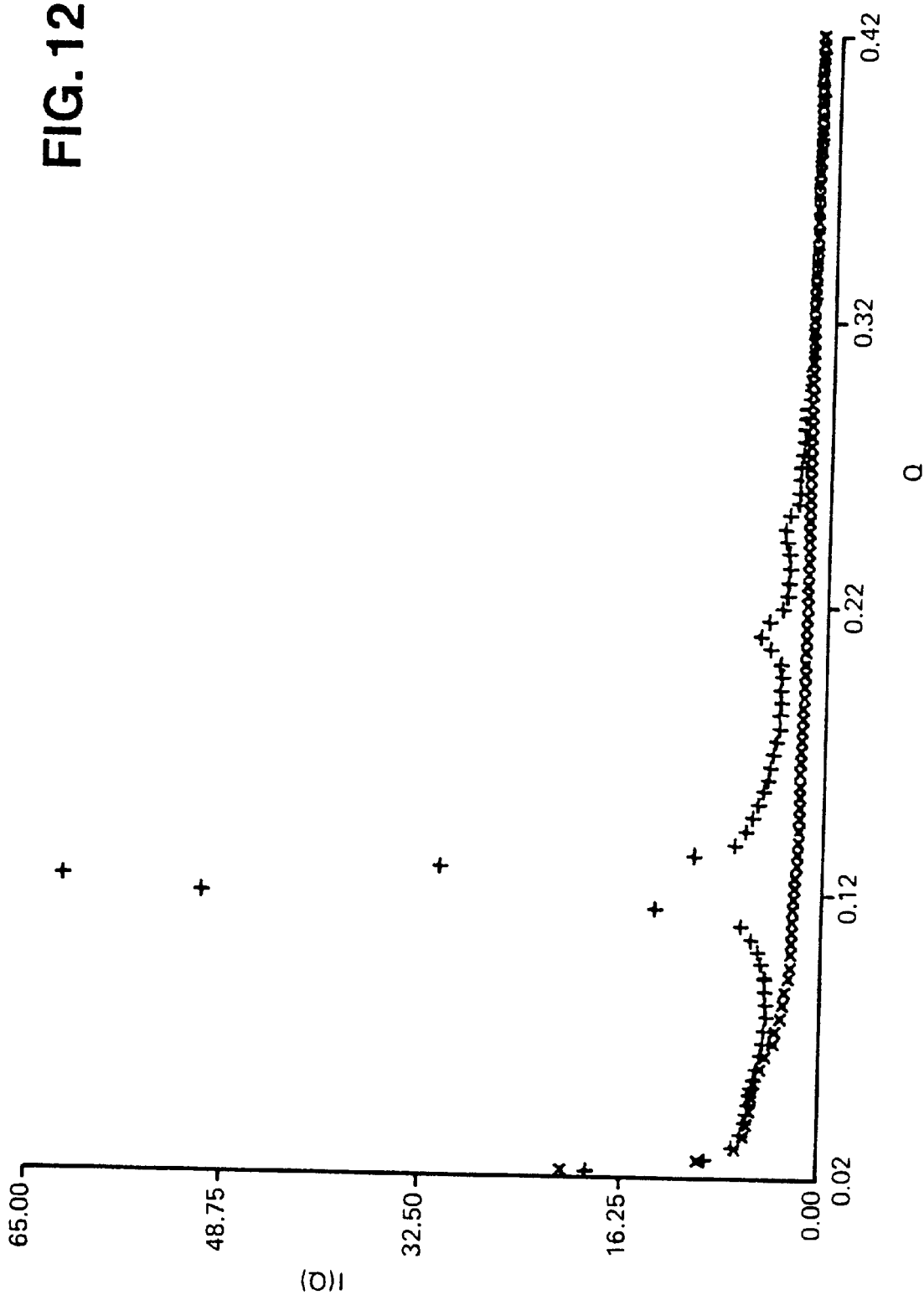
Figure 13:
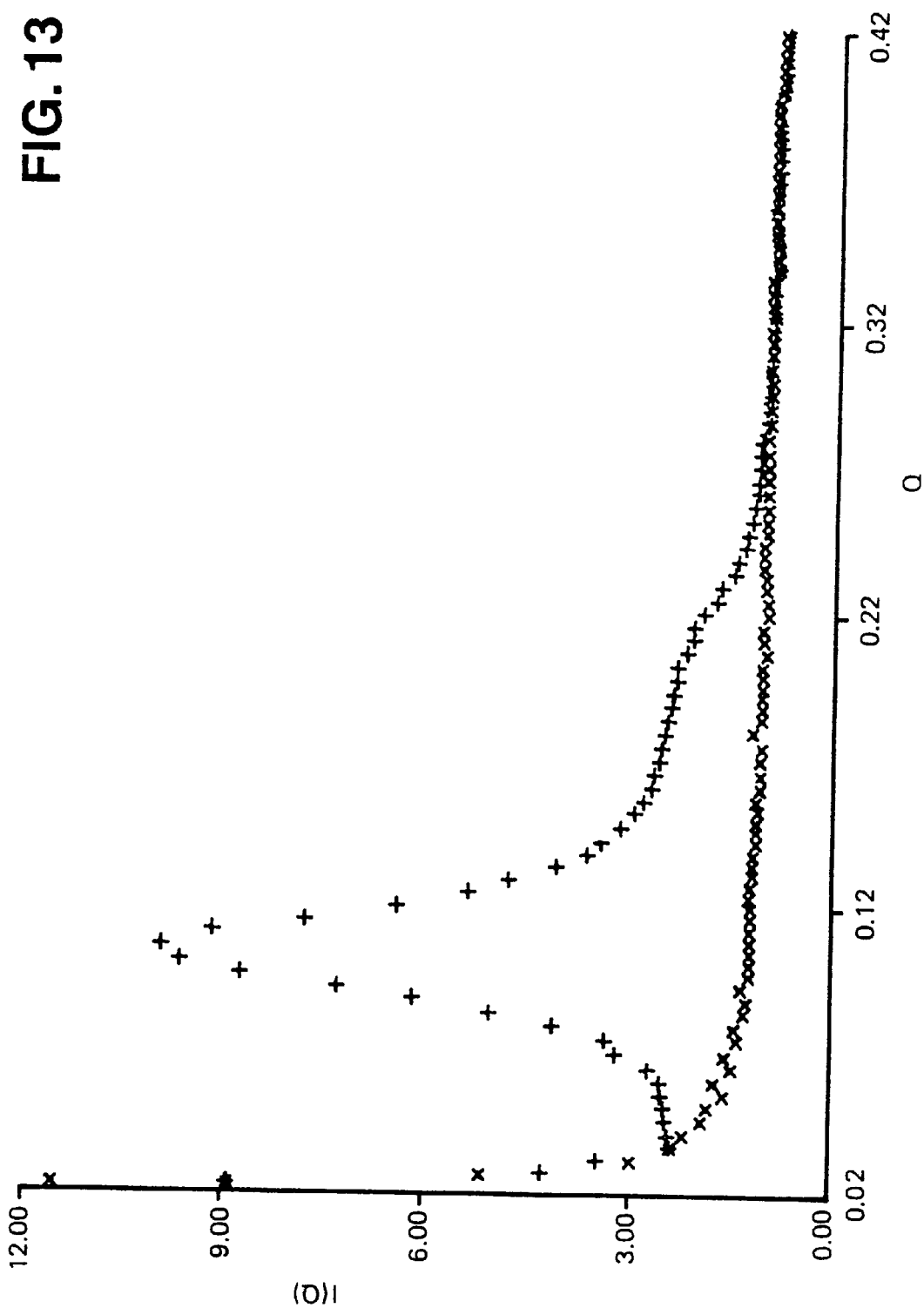
Figure 14:
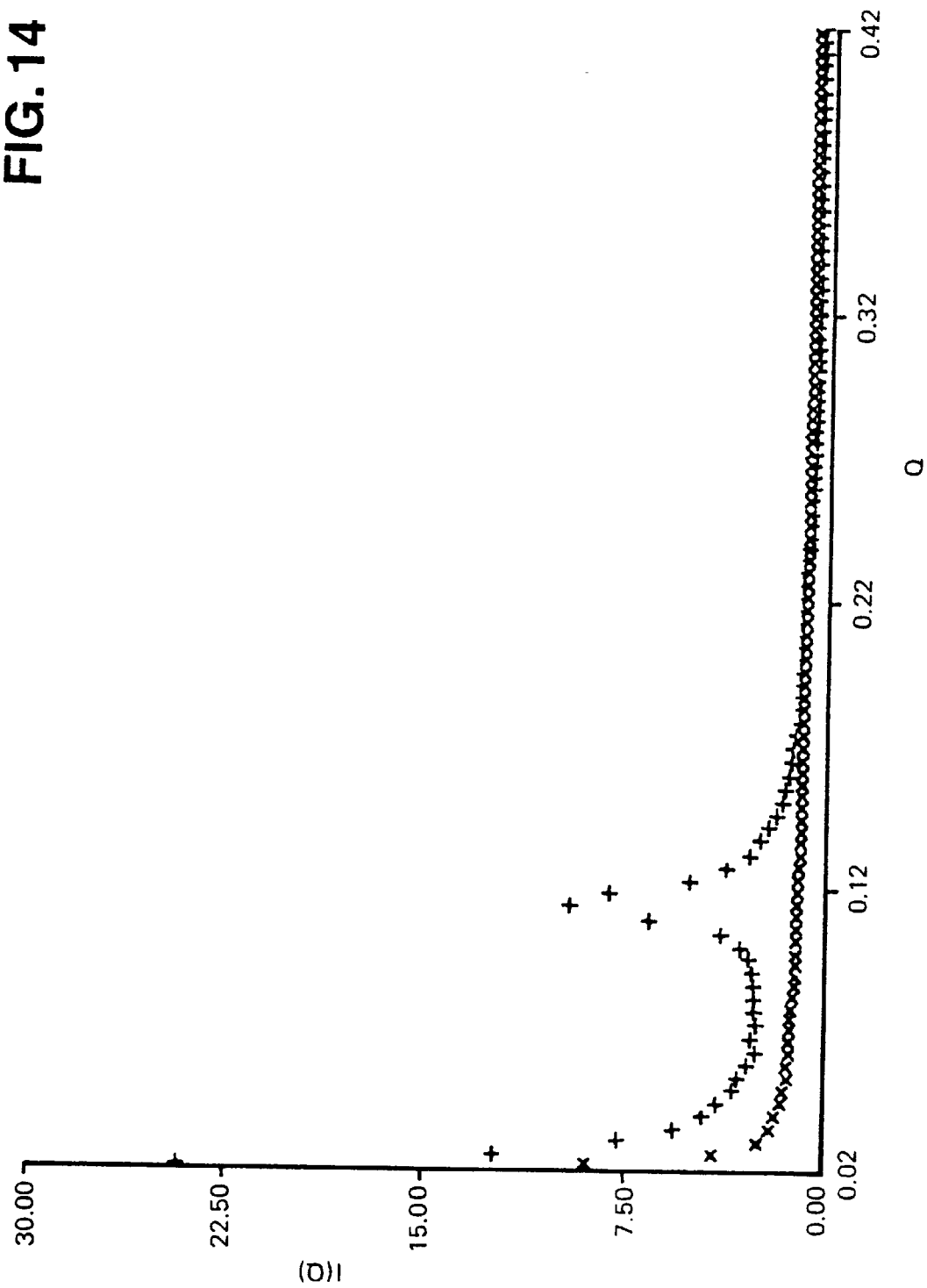
Figure 15:
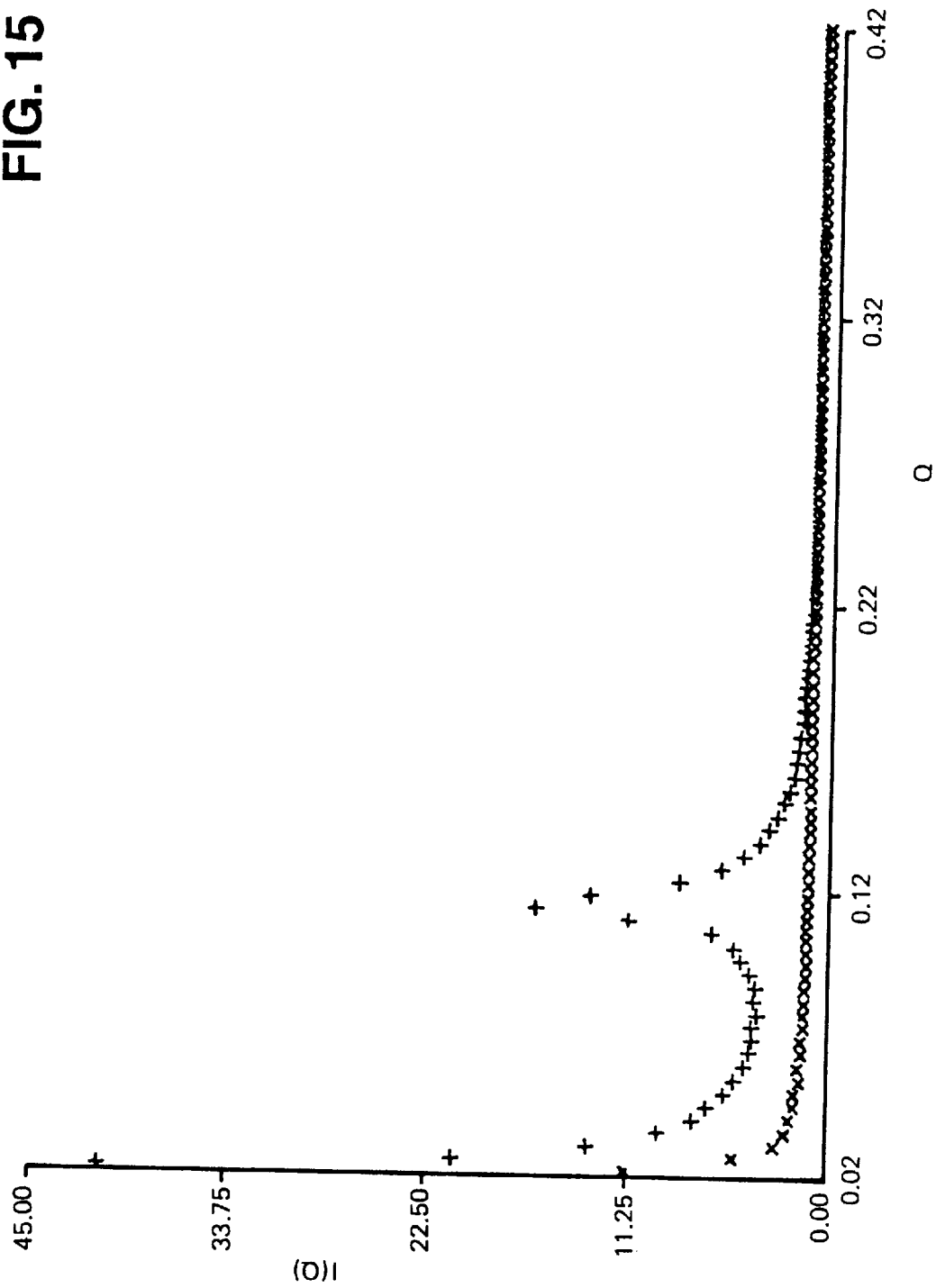
Figure 16:
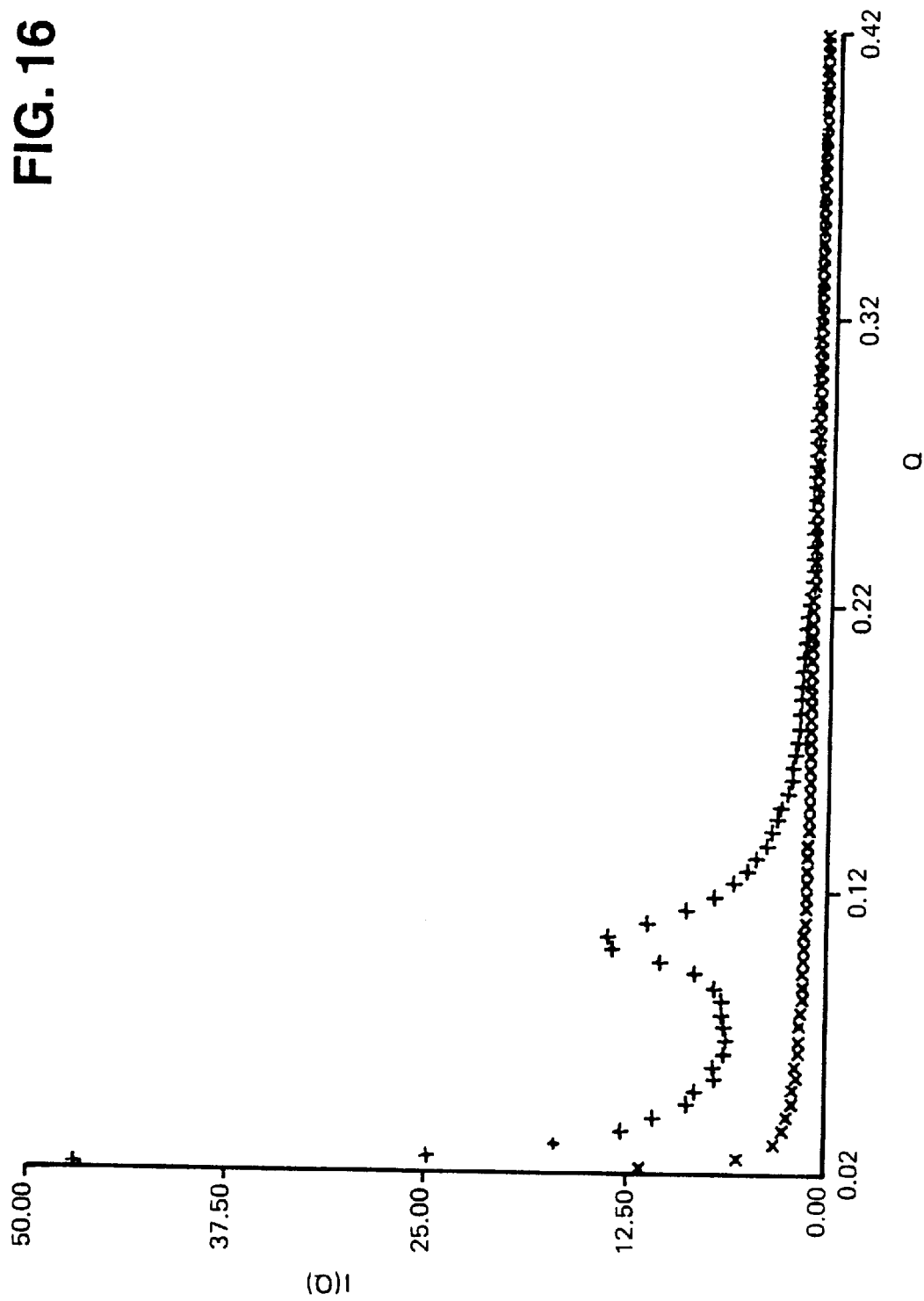
Figure 17:
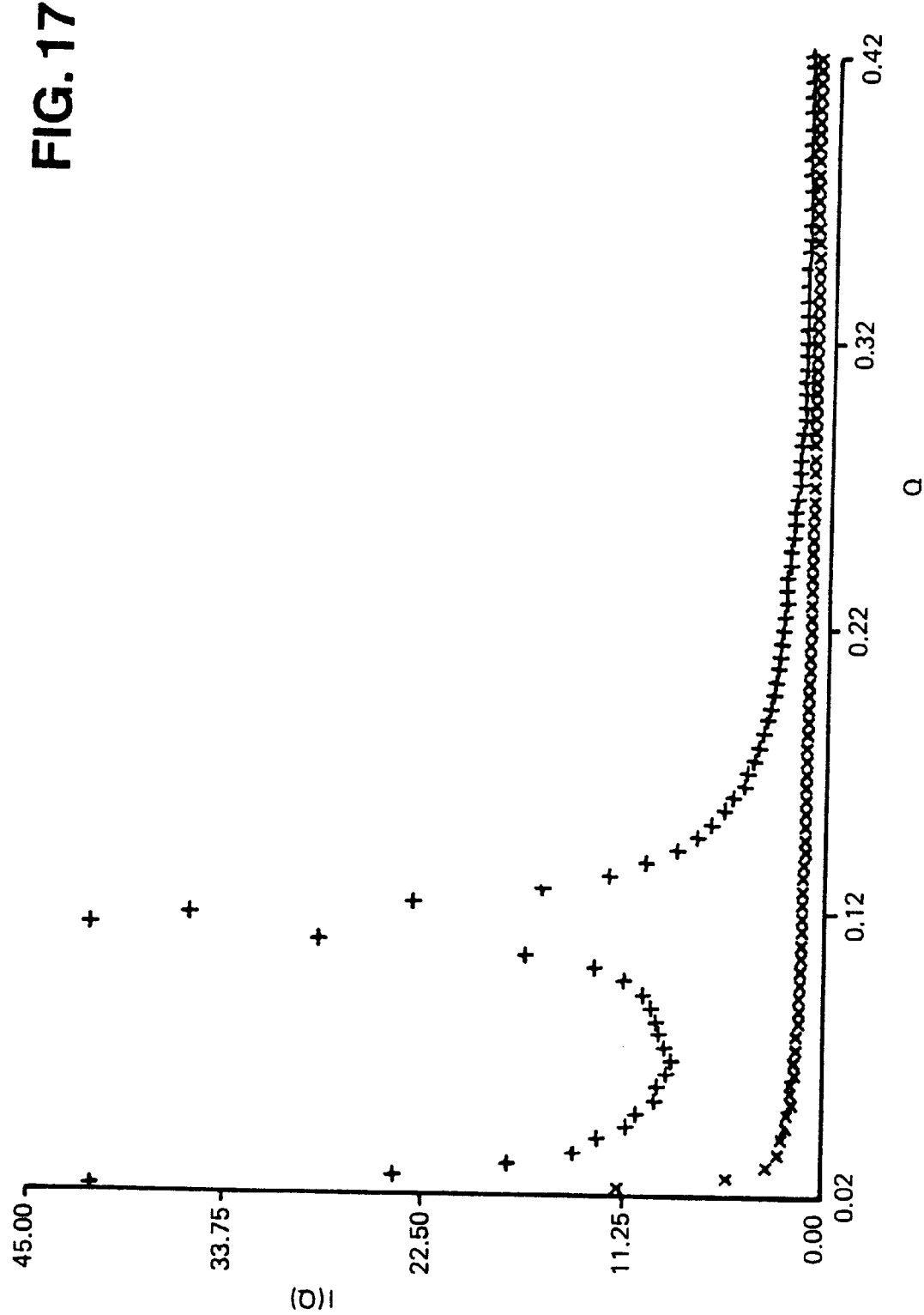
Figure 18:
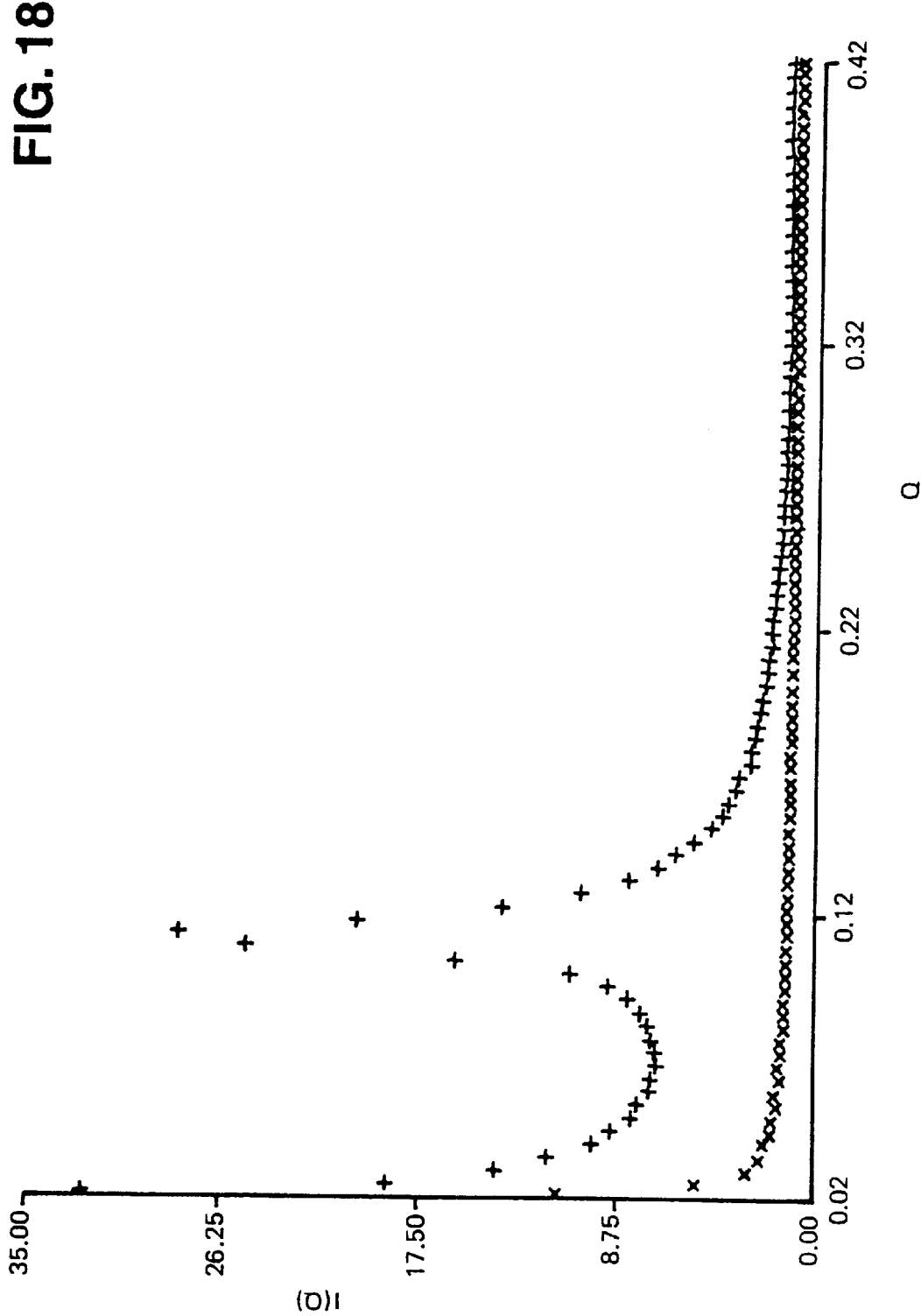

Certain of the compositions were examined by small angle X-ray diffraction. In the case of Examples 6', 8', 11', 12' and 13' the X-ray spectrum was plotted based on the pourable, hexagonal phase composition i.e. the composition as shown in the Tables but without the addition of the electrolyte (sodium carbonate). In the case of Examples 14' and 15', sufficient sodium hydroxide was included to neutralise the free acids. All other X-ray diffraction examples are based on the complete formulations as given. The drawings, FIGS. 1 to 18 are plots of the X-ray diffraction spectra as set out in Table 7'. FIG. 4 is a contour plot which illustrates an alignment of scattering. In most other cases the scattering was evenly distributed around the unscattered beam. In each of the drawings "+" plots are of the sample and "X" plots were of the empty sample cell plotted alongside the sample for comparison. In each case a large peak was visible having a momentum transfer value corresponding to the presence of a repeating structural feature with a repeat spacing between 4 and 10 nm.

In the case of the electrolyte-free (pourable hexagonal phases), there were two substantially smaller peaks at respectively 3$^{-0.5}$ and half the spacing of the first peak, which we attribute to higher order effects. Even higher order peaks are detectable in some samples. These spacings are attributable to a hexagonal symmetry.

In the case of Example 14', the addition of sodium hydroxide has forced a change in the structure. A peak corresponding to a structural feature with a repeat spacing of 19.4 nm is accompanied by second and third order peaks, indicating a lamellar structure.

The clear isotropic liquids, examples 16', 17' and 18', each display a single relatively broad peak with no clear evidence of higher order scattering. Example 19 shows some indication of a second order scattering, suggesting the presence of a lamellar or spherulitic structure.

The spherulitic suspending media, Examples 23' and 24' are zeolite containing built detergent liquids. Examples 21' and 22' each gave a stronger, sharper main peak than the clear liquids, but with no clear higher order features. The electron and optical micrographs show them to comprise well-defined spherulites.

The following abreviations set out in Table 1 will be used in the ensuing tables.

TABLE 1'

| | |
|---|---|
| LABS | is sodium $C_{10-14}$ alkyl benzene sulphonate; |
| KSN | is sodium $C_{12-18}$ alkyl three mole ethyleneoxy sulphate (mean mole weight 440); |
| OB | is lauryl/myristyl trimethyl amine oxide; |
| TEA | is triethanolamine; |
| CDE | is coconut diethanolamide; |
| CME | is coconut monoethanolamide; |
| KCMP | is $C_{12-14}$ alcohol with 10 mole average ethylene oxide; |
| SDTP | is sodium diethylenetriamine penta(methylenephosphanate); |
| CBS/X | is a proprietary optical brightner sold under the Registered; Trademark "TINOPAL CBS/X"; |
| SXS | is sodium xylene sulphonate, 93% active; |
| KL 6 | is cetyl/oleyl alcohol six mole ethoxylate; |
| KC 8 | is $C_{12-18}$ alcohol eight mole ethoxylate; |
| KC 3 | is $C_{12-18}$ alcohol three mole ethoxylate |
| LP 2 | is coconut monoethanolamide two mole ethoxylate; |
| 91-2.5 | is a $C_{9-11}$ alcohol with 2.5 moles average ethylene oxide; |
| 91-5 | is $C_{9-11}$ alcohol with five moles average ethylene oxide; |
| 23-6.5 | is $C_{12-13}$ alcohol with six point five moles average ethylene oxides; |
| 91-8 | is $C_{9-11}$ alcohol with eight moles average ethylene oxide; |
| 91-l2 | is $C_{9-11}$ alcohol with twelve moles average ethylene oxides. |
| 190 | is a silicone/glycol copolymer, sold by Dow Corning under the Registered Trade Mark "DC" 190; |
| 7908 | is a fatty acid sold by Unichema under the Registered Trade Mark "PRIFAC" 7908; |
| PFKA | is palm kernel fatty acid; |
| CFA | is coconut fatty acid |
| HTA | is hard tallow acid |
| LFA | is lauric fatty acid |
| S132 | is a silicone antifoam. |

TABLE II'

| EXAMPLE | 1' | 2' | 3' | 4' | 5' | 6' | 7' | 8' |
|---|---|---|---|---|---|---|---|---|
| LABS | 6 | 5 | 5 | 5 | 5 | 5 | 5 | 5 |
| KSN | 12 | 12 | 12 | 12 | 12 | 12 | 12 | 12 |
| 91-2.5 | 4 | 4 | 4 | 4 | 4 | 4 | 4 | 4 |
| 91-12 | 2 | 2 | 2 | 2 | 2 | 2 | 2 | 2 |
| OB | — | 1 | — | — | — | — | — | — |
| CDE | — | — | 1 | — | — | — | — | — |
| CME | — | — | — | 1 | — | — | — | 1 |
| KCMP | — | — | — | — | 1 | — | 1 | — |
| HTA | — | — | — | — | — | 1 | — | — |
| CFA | 10 | 10 | 10 | 10 | 10 | 10 | 10 | 10 |
| TEA | 5 | 5 | 5 | 5 | 5 | 5 | 5 | 5 |
| Na$_2$CO$_3$ | 4.6 | 4.6 | 4.6 | 4.6 | 4.6 | 4.6 | 4.6 | 4.6 |
| SDTP | 1 | 1 | 1 | 1 | 1 | 1 | 1.5 | 1.5 |
| CBS/X | 0.2 | 0.2 | 0.2 | 0.2 | 0.2 | 0.2 | 0.2 | 0.2 |
| SXS | 0.5 | 0.5 | 0.5 | 0.5 | 0.5 | 0.5 | 0.5 | 0.5 |
| Perfume | 0.4 | 0.4 | 0.4 | 0.4 | 0.4 | 0.4 | 0.4 | 0.4 |
| Protease | 0.2 | 0.2 | 0.2 | 0.2 | 0.2 | 0.2 | 0.2 | 0.2 |
| Viscosity 54/100 (cps) | 510 | 550 | 520 | 600 | 500 | 580 | 420 | 440 |

TABLE III'

| EXAMPLE | 9' | 10' | 11' | 12' | 13' | 14' | 15' | 16' |
|---|---|---|---|---|---|---|---|---|
| hard tallow acid | 6.0 | — | — | — | — | — | — | — |
| KL6 | — | 6.0 | — | — | — | — | — | — |
| CDE | — | — | 6.0 | — | — | — | — | — |
| KC8 | — | — | — | 6.0 | — | — | — | — |
| CME | — | — | — | — | 6.0 | — | — | — |
| LP2 | — | — | — | — | — | 6.0 | — | — |
| KCMP | — | — | — | — | — | — | 6.0 | — |
| OB | — | — | — | — | — | — | — | 6.0 |
| KSN | 12.0 | 12.0 | 12.0 | 12.0 | 12.0 | 12.0 | 12.0 | 12.0 |
| 91-2.5 | 4.0 | 4.0 | 4.0 | 4.0 | 4.0 | 4.0 | 4.0 | 4.0 |
| 91-12 | 2.0 | 2.0 | 2.0 | 2.0 | 2.0 | 2.0 | 2.0 | 2.0 |
| CFA | 10.0 | 10.0 | 10.0 | 10.0 | 10.0 | 10.0 | 10.0 | 10.0 |
| TEA | 5.0 | 5.0 | 5.0 | 5.0 | 5.0 | 5.0 | 5.0 | 5.0 |
| $Na_2CO_3$ | 4.46 | 4.5 | 4.6 | 4.8 | 4.6 | 4.7 | 4.8 | 4.7 |
| CBS/X | 0.2 | 0.2 | 0.2 | 0.2 | 0.2 | 0.2 | 0.2 | 0.2 |
| SXS | 0.5 | 0.5 | 0.5 | 0.5 | 0.5 | 0.5 | 0.5 | 0.5 |
| Perfume | 0.4 | 0.4 | 0.4 | 0.4 | 0.4 | 0.4 | 0.4 | 0.4 |
| Protease | 0.2 | 0.2 | 0.2 | 0.2 | 0.2 | 0.2 | 0.2 | 0.2 |
| pH | 9.01 | 9.00 | 9.00 | 9.01 | 9.00 | 8.99 | 8.98 | 9.00 |
| Viscosity 54/(cP) | 770 | 1380 | 930 | 1190 | 620 | 300 | 420 | 1600 |

TABLE IV'

| EXAMPLE | 17' | 18' | 19' | 20' | 21' | 22' | 23' | 24' | 25' |
|---|---|---|---|---|---|---|---|---|---|
| LABS | 6 | 6 | 6 | 6 | 6 | 6 | 7 | 7 | 6 |
| KSN | 12 | 12 | 12 | 12 | 12 | 12 | 13 | 13 | 12 |
| 91-2.5 | 4 | 5 | 4 | 5 | 4 | 3 | 4 | 2 | 4 |
| 91-5 | — | — | — | — | — | — | — | — | — |
| 91-12 | 2 | 1 | 2 | 1 | 2 | 3 | 4 | 4 | 2 |
| CFA | 10 | 10 | 10 | 10 | 10 | 10 | 10 | 10 | 10 |
| TEA | 5 | 5 | 5 | 5 | 5 | 5 | 5 | 5 | 5 |
| $Na_2CO_3$ | 4.5 | 4.2 | 4.3 | 4.5 | 4.5 | 4.6 | 4.5 | 4.3 | 4.3 |
| CBS/X | 0.2 | 0.2 | 0.2 | 0.2 | 0.2 | 0.2 | 0.2 | 0.2 | 0.2 |
| SXS | 0.5 | 0.5 | 0.5 | 1.0 | 1.0 | 1.0 | 1.5 | 1.5 | 1.5 |
| Perfume | 0.4 | 0.2 | 0.2 | 0.2 | 0.2 | 0.2 | 0.2 | 0.2 | 0.2 |
| Protease | 0.2 | — | — | — | — | — | — | — | — |
| Solids | 45.3 | 44.1 | 44.2 | 44.9 | 44.9 | 45.0 | 49.4 | 47.2 | 45.2 |

TABLE V'

| EXAMPLE | 26' | 27' | 28' | 29' | 30' | 31' | 32' | 33' | 34' |
|---|---|---|---|---|---|---|---|---|---|
| LABS | 6.0 | 5.0 | 5.0 | 5.0 | 5.0 | 5.0 | 5.0 | 5.0 | 5.0 |
| KSN | 12.0 | 10.0 | 10.0 | 10.0 | 10.0 | 10.0 | 10.0 | 10.0 | 10.0 |
| 91-2.5 | — | — | — | — | 5.0 | — | — | — | — |
| 91-5 | — | — | — | 5.0 | — | 5.0 | — | — | — |
| 23-8.5 | — | — | 5.0 | — | — | — | 5.0 | — | — |
| 91-8 | — | 5.0 | — | — | — | — | — | 5.0 | — |
| 91-12 | 6.0 | — | — | — | — | — | — | — | 5.0 |
| CFA | 10.0 | 10.0 | 10.0 | 10.0 | 10.0 | 10.0 | 10.0 | 10.0 | 10.0 |
| TEA | 5.0 | 5.0 | 5.0 | 5.0 | 5.0 | — | — | — | — |
| NaOH | — | — | — | — | 4.0 | 4.0 | 3.9 | 4.2 | — |
| $Na_2CO_3$ | 4.2 | 4.6 | 4.4 | 4.3 | 3.5 | — | — | — | — |
| CBS/X | 0.2 | 0.2 | 0.2 | 0.2 | 0.2 | 0.2 | 0.2 | 0.2 | 0.2 |
| Solids | 43.4 | 39.8 | 39.6 | 39.5 | 38.7 | 34.2 | 34.2 | 34.1 | 34.4 |
| Viscosity 100 RVT | 940 | 480 | 1150 | 970 | 1460 | 310 | 180 | 130 | 90 |

TABLE VI'

| EXAMPLE | 35' | 36' | 37' | 38' |
|---|---|---|---|---|
| LABS | 5.0 | 5.0 | 5.0 | 5.0 |
| KSN | 10.0 | 10.0 | 10.0 | 10.0 |
| 25-7 | 5.0 | 5.0 | 5.0 | 5.0 |
| CFA | 10.0 | — | 10.0 | — |
| LFA | — | 10.0 | — | 10.0 |
| CBS/X | 0.2 | 0.2 | 0.2 | 0.2 |
| Water | | balance | | |
| TEA | 5.0% | 5.0% | — | — |
| Sodium hydroxide | — | — | 4.03% | 4.12% |
| Sodium carbonate | 4.3% | 4.3% | — | — |
| pH | 9.0% | 8.99 | 9.00 | 8.99 |
| 1% pH | 5.54 | 8.38 | 8.50 | 7.77 |
| Appearance | | Clear mobile liquid | | |

The foregoing Examples 35' to 38' were made by mixing the aqueous surfactants and optical brightener to form a G-phase and then adding the bases.

EXAMPLE 39'

The following ingredients were mixed, the coconut fatty acid being added last to avoid forming a G-phase.

| LABS | 5% |
|---|---|
| KSN | 12% |
| 91-2.5 | 4% |
| 91-12 | 2% |
| OB | 1% |
| CFA | 10% |
| TEA | 5% |
| Potassium carbonate | 5.5% |
| SDTP | 1% |
| CBS-X | 0.2% |
| SX-93 | 0.5% |
| Perfume | 0.4% |
| Enzyme | 0.2% |
| Blue + Green dye | 0.42% |
| opacifier | 0.5% |

EXAMPLE 40'

The following ingredients were mixed in the order shown:

| % w/w | |
|---|---|
| 7.8 | KSN |
| 0.14 | CBSX |
| 0.49 | 190 |
| 19.81 | zeolite |
| 3.42 | LABS |
| 0.48 | SXS |
| 3.42 | TEA |
| 3.9 | Potassium carbonate |
| 0.68 | SDTP |
| 3.9 | KC3 |
| 0.48 | OB |
| 6.83 | 7908 |
| 10.90 | trisodium citrate |
| 0.2 | S132 |
| 0.35 | perfume |

At each stage of mixing, just sufficient water was added to maintain a mobile stirrable mixture, and the final mixture was diluted with water to provide a total water content sufficient to make the balance to 100% in the above table.

The composition had a conductance at 20° C. of 9.04 $mScm^{-1}$ and a viscocity at 20° C. measured on a Brookfield RVT Viscometer, Spindle 5, speed 100 of 2Ps.

A 1% w/w aqueous solution had a pH of 9.4.

The composition was opaque, spherulitic and showed no sedimentation after standing for three months at ambient temperature.

EXAMPLES 41'–45'

The formulations in the table VII' below were made up. The products were stable, homogeneous, opaque, mobile, spherulitic compositions. Into one sample of Example 41' was stirred 20% by weight of a zeolite detergent builder. The resulting composition was stable to storage at ambient temperature after three months.

Each of examples 41' to 44' was diluted by slowly adding an equal volume of water with stirring. The compositions diluted readily, without any sign of gel formation for form clear aqueous solutions. Example 45' was a stable opaque suspension, which did not sediment after 3 months at laboratory ambient temperature.

TABLE VII'

| EXAMPLE NO. | 41' | 42' | 43' | 44' | 45' |
| --- | --- | --- | --- | --- | --- |
| LABS | 3.0 | 3.0 | 3.02 | 3.02 | 2.5 |
| $C_{9/11}$ alkyl sulphate | 3.0 | 3.0 | 3.02 | 3.02 | 2.5 |
| KSN | 14.3 | 14.42 | 14.52 | 14.54 | 10.9 |
| 91-12 | 1.2 | 1.2 | 1.21 | 1.21 | 0.95 |
| 91-2.5 | 3.0 | 3.0 | 3.02 | 3.02 | 2.5 |
| PKFA | 3.0 | 3.0 | 3.02 | 3.02 | 2.5 |
| SXS | 0.6 | — | 0.61 | — | 0.5 |
| TEA | 1.8 | — | 1.82 | — | 1.3 |
| Optical Brightner | 0.1 | 0.1 | 0.1 | 0.1 | 0.2 |
| Perfume | 0.5 | 0.5 | 0.5 | 0.2 | 0.5 |
| Dye | 0.01 | 0.01 | 0.01 | 0.01 | — |
| Potassium carbonate | 10.6 | 9.82 | 7.67 | 7.66 | 9.0 |
| Potassium hydrogen carbonate | — | — | 5.56 | 5.55 | — |
| Formalin | 0.075 | 0.08 | 0.08 | 0.08 | 0.075 |
| Zeolite | — | — | — | — | 20.00 |
| Sodium chloride | — | — | — | — | 1.0 |
| Water | | | Balance | | |
| Viscosity *Pa · s | 0.64 | 1.12 | 0.96 | 0.88 | 1.0 |
| pH (0.2% w/waq.) | 10.00 | 9.71 | 9.5 | 9.6 | 10.8 |
| s.g. $gcm^{-3}$ | 1.072 | 1.060 | 1.045 | 0.979 | 1.25 |

*Measured an Brookfield RVT (Spindle 4) at speed setting 100.

EXAMPLE 46'

Eight compositions each comprising 2 parts KSN to one part LABS by weight, at a total surfactant concentration of 30% by weight were prepared containing progressively increasing concentrations of potassium carbonate, from 2 to 12% by weight. The conductivity, viscosity and d-spacing of the principal X-ray diffraction peak were measured.

The results are given in Table VIII'

TABLE VIII'

| % CARBONATE | VISCOSITY | CONDUCTIVITY | d-SPACING |
| --- | --- | --- | --- |
| 2 | >2 Pa · s | 30 $mScm^{-1}$ | 58 nm |
| 4 | 1.7 | 24 | 60 |
| 6 | 1.5 | 18 | 76 |
| 8 | >2 | 6 | 82 |
| 9 | 1.4 | 6 | 75 |
| 9.5 | 1 | 6.5 | 68 |
| 10 | 0.3 | 12 | 40 |
| 12 | — | — | 46 |

Compositions containing from 8.5 to 10.5% of potassium carbonate were found to provide stable spherulitic formulations. Compositions containing less than 3% by weight were immobile or viscous anisotropic hexagonal phases. Compositions containing 3 to 7% by weight carbonate were substantially clear, Newtonian liquids, whose viscosity increased on dilution. Compositions containing from 7.5 to 8% by weight carbonate underwent phase separation, into an aqueous layer and a lamellar surfactant layer.

EXAMPLE 47'

An aqueous composition was prepared comprising:

| | |
| --- | --- |
| KSN | 10.4 |
| PKFA | 13.8 |
| TEA | 6.8 |
| LABS | 10.4 |
| Sodium Citrate dihydrate | 10.4 |
| Potassium Carbanate | 4.0 |

The composition was a stable, mobile, translucent, lamellar, liquid crystal detergent. It had good washing properties and was readily dilutable without gel formation. The composition was capable of suspending zeolite builder. A sample was mixed with 20% by weight of zeolite and provided a stable cream which showed no sign of separation over three months storage at ambient temperature.

What is claimed is:

1. A liquid detergent composition consisting of: water; from 5% to 9% by weight of alkyl ether sulphate; from 3% to 8% by weight of surfactants selected from the group consisting of alkyl benzene sulphonate and alkyl sulphate; from 0% to 5% by weight of soap; from 0% to 3% by weight of ethoxylated alcohol non-ionic surfactant; and from 2% to 8% by weight of sodium and/or potassium carbonate, said detergent composition having a viscosity which rises on dilution with water to a maximum and then falls with further dilution.

2. A liquid detergent composition consisting of water, from 10% to 15% by weight of sodium alkyl ether sulphate, from 4% to 10% by weight of surfactants selected from the group consisting of sodium alkyl benzene sulphonate and sodium alkyl sulphate, from 0% to 6% by weight soap, from 0% to 3% by weight ethoxylated non-ionic surfactant and from 8.5% to 12% by weight of sodium and/or potassium carbonate being a quantity sufficient to form a stable spherulitic composition.

* * * * *